(12) United States Patent
Strommer et al.

(10) Patent No.: US 8,936,559 B2
(45) Date of Patent: *Jan. 20, 2015

(54) SENSOR MOUNTED FLEXIBLE GUIDEWIRE

(71) Applicant: MediGuide, Ltd., Haifa (IL)

(72) Inventors: Gera Strommer, Haifa (IL); Uzi Eichler, Haifa (IL); Ran Sela, Tel Aviv-Yafo (IL); Nimrod Meller, Kiryat Tivon (IL); Lior Sobe, Kadima (IL); Aharon Gildin, Haifa (IL)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/729,694

(22) Filed: Dec. 28, 2012

(65) Prior Publication Data

US 2013/0102892 A1   Apr. 25, 2013

Related U.S. Application Data

(63) Continuation of application No. 12/357,971, filed on Jan. 22, 2009, now Pat. No. 8,343,076.

(60) Provisional application No. 61/028,665, filed on Feb. 14, 2008, provisional application No. 61/023,007, filed on Jan. 23, 2008.

(51) Int. Cl.
*A61B 5/00* (2006.01)
*A61M 25/00* (2006.01)
(Continued)

(52) U.S. Cl.
CPC . *A61B 5/065* (2013.01); *A61B 5/06* (2013.01); *A61B 5/6851* (2013.01); *A61M 25/09* (2013.01); *A61M 25/0905* (2013.01); *A61B 2017/22042* (2013.01); *A61B 2019/5251* (2013.01); *A61M 2025/0002* (2013.01);
(Continued)

(58) Field of Classification Search
CPC .............. A61M 25/0054; A61M 25/0127; A61M 2025/0166; A61M 2025/09083; A61B 33/34084; A61B 33/34053; A61B 5/6851
USPC .......................... 600/585, 410, 411
See application file for complete search history.

(56) References Cited

U.S. PATENT DOCUMENTS 35,648 A * 6/1862 Dyer ............................. 209/37
2,452,679 A  11/1948 Ramsden
(Continued)

FOREIGN PATENT DOCUMENTS

EP   0894473   2/1999
JP   08-112289   5/1996
(Continued)

*Primary Examiner* — Sean Dougherty
(74) *Attorney, Agent, or Firm* — Dykema Gossett PLLC

(57) ABSTRACT

A flexible guidewire comprising a hollow tube, having a proximal section and a distal section, the distal section having a distal tip, the outer diameter of the distal section gradually decreasing toward the distal tip, the outer diameter of the distal tip being larger than the smallest outer diameter of the distal section, the flexible guidewire further comprising a plug coupled with the distal tip of the hollow tube for creating a non-traumatic tip, and the flexible guidewire further comprising a tubular spring, being place around the distal section of the hollow tube for maintaining the outer diameter of the hollow tube over the length thereof and for supporting compressive loads.

20 Claims, 15 Drawing Sheets

(51) Int. Cl.
  *A61M 25/09* (2006.01)
  *A61B 5/05* (2006.01)
  *A61B 5/06* (2006.01)
  *A61B 17/22* (2006.01)
  *A61B 19/00* (2006.01)

(52) U.S. Cl.
  CPC ............... *A61M 2025/09083* (2013.01); *A61M 2025/09108* (2013.01); *A61M 2025/09133* (2013.01); *A61M 2025/0915* (2013.01); *A61M 2025/09175* (2013.01); *A61M 2205/3515* (2013.01); *H01R 2201/12* (2013.01)
  USPC ........................... 600/585; 600/410; 600/411

(56) References Cited

U.S. PATENT DOCUMENTS

| | | | |
|---|---|---|---|
| 2,483,900 A | 10/1949 | Hardenberg et al. | |
| 4,873,986 A | 10/1989 | Wallace | |
| 4,991,602 A | 2/1991 | Amplatz et al. | |
| 5,386,828 A | 2/1995 | Owens et al. | |
| 5,445,151 A | 8/1995 | Darrow et al. | |
| 5,501,228 A | 3/1996 | Lafontaine et al. | |
| RE35,648 E | 11/1997 | Tenerz et al. | |
| 5,728,062 A | 3/1998 | Brisken | |
| 5,850,682 A | 12/1998 | Ushiro | |
| 5,868,674 A | 2/1999 | Glowinski et al. | |
| 5,873,835 A * | 2/1999 | Hastings et al. | 600/488 |
| 6,007,478 A * | 12/1999 | Siess et al. | 600/16 |
| 6,090,052 A | 7/2000 | Akerfeldt et al. | |
| 6,106,486 A | 8/2000 | Tenerz et al. | |
| 6,112,598 A | 9/2000 | Tenerz et al. | |
| 6,142,958 A | 11/2000 | Hammarstrom et al. | |
| 6,261,246 B1 | 7/2001 | Pantages et al. | |
| 6,353,379 B1 | 3/2002 | Busletta et al. | |
| 6,375,606 B1 | 4/2002 | Garibaldi et al. | |
| 6,428,336 B1 | 8/2002 | Akerfeldt | |
| 6,428,489 B1 | 8/2002 | Jacobsen et al. | |
| 6,442,413 B1 | 8/2002 | Silver | |
| 6,675,033 B1 | 1/2004 | Lardo et al. | |
| 6,711,429 B1 | 3/2004 | Gilboa et al. | |
| 6,847,837 B1 | 1/2005 | Melzer et al. | |
| 6,862,467 B2 | 3/2005 | Moore et al. | |
| 7,011,636 B2 | 3/2006 | Tenerz | |
| 7,048,716 B1 | 5/2006 | Kucharczyk et al. | |
| 7,130,700 B2 * | 10/2006 | Gardeski et al. | 607/122 |
| 7,162,293 B2 | 1/2007 | Weiss | |
| 7,169,118 B2 | 1/2007 | Reynolds et al. | |
| 7,186,209 B2 | 3/2007 | Jacobson et al. | |
| 7,197,354 B2 | 3/2007 | Sobe | |
| 7,645,233 B2 | 1/2010 | Tulkki et al. | |
| 7,951,081 B2 * | 5/2011 | Hamm et al. | 600/437 |
| 8,239,003 B2 | 8/2012 | Akins | |
| 8,343,076 B2 | 1/2013 | Sela | |
| 8,579,825 B2 * | 11/2013 | Tenerz et al. | 600/488 |
| 2001/0051769 A1 | 12/2001 | Hoek et al. | |
| 2002/0009535 A1 | 1/2002 | Michal et al. | |
| 2002/0032390 A1 | 3/2002 | Jafari | |
| 2003/0028128 A1 | 2/2003 | Tenerz | |
| 2003/0073898 A1 | 4/2003 | Weiss | |
| 2003/0120146 A1 | 6/2003 | Dumoulin | |
| 2003/0120148 A1 | 6/2003 | Pacetti | |
| 2003/0139689 A1 | 7/2003 | Shturman et al. | |
| 2003/0199852 A1 | 10/2003 | Seward et al. | |
| 2003/0220588 A1 | 11/2003 | Tenerz et al. | |
| 2004/0102720 A1 | 5/2004 | Kellerman et al. | |
| 2004/0116800 A1 | 6/2004 | Helfer et al. | |
| 2004/0167436 A1 | 8/2004 | Reynolds et al. | |
| 2004/0167442 A1 | 8/2004 | Shireman et al. | |
| 2004/0220462 A1 | 11/2004 | Schwartz | |
| 2004/0254458 A1 | 12/2004 | Govari | |
| 2004/0260172 A1 | 12/2004 | Ritter et al. | |
| 2005/0049523 A1 * | 3/2005 | Crank | 600/585 |
| 2005/0059852 A1 | 3/2005 | Rioux et al. | |
| 2005/0070793 A1 * | 3/2005 | Pacetti et al. | 600/431 |
| 2006/0178576 A1 | 8/2006 | Weber et al. | |
| 2007/0185386 A1 | 8/2007 | Cheng | |
| 2007/0208251 A1 | 9/2007 | Anderson et al. | |
| 2007/0255144 A1 * | 11/2007 | Tulkki et al. | 600/481 |
| 2007/0255145 A1 * | 11/2007 | Smith et al. | 600/485 |
| 2008/0097247 A1 | 4/2008 | Eskuri | |
| 2009/0112128 A1 | 4/2009 | Schiff et al. | |
| 2009/0143777 A1 | 6/2009 | Pacey et al. | |
| 2009/0177119 A1 | 7/2009 | Heidner et al. | |
| 2009/0209900 A1 | 8/2009 | Carmeli et al. | |
| 2010/0217275 A1 * | 8/2010 | Carmeli et al. | 606/128 |
| 2010/0286536 A1 | 11/2010 | Samuelsson | |
| 2011/0152721 A1 | 6/2011 | Sela | |
| 2012/0203118 A1 | 8/2012 | Samuelsson | |
| 2012/0265079 A1 | 10/2012 | Hilmersson | |
| 2013/0102892 A1 | 4/2013 | Strommer | |
| 2013/0102927 A1 | 4/2013 | Hilmersson | |
| 2013/0338538 A1 | 12/2013 | Park | |
| 2014/0276138 A1 | 9/2014 | Millett | |

FOREIGN PATENT DOCUMENTS

| | | |
|---|---|---|
| JP | 2003-024447 | 1/2003 |
| JP | 2006-150082 | 6/2006 |
| WO | 96/05768 | 2/1996 |

* cited by examiner

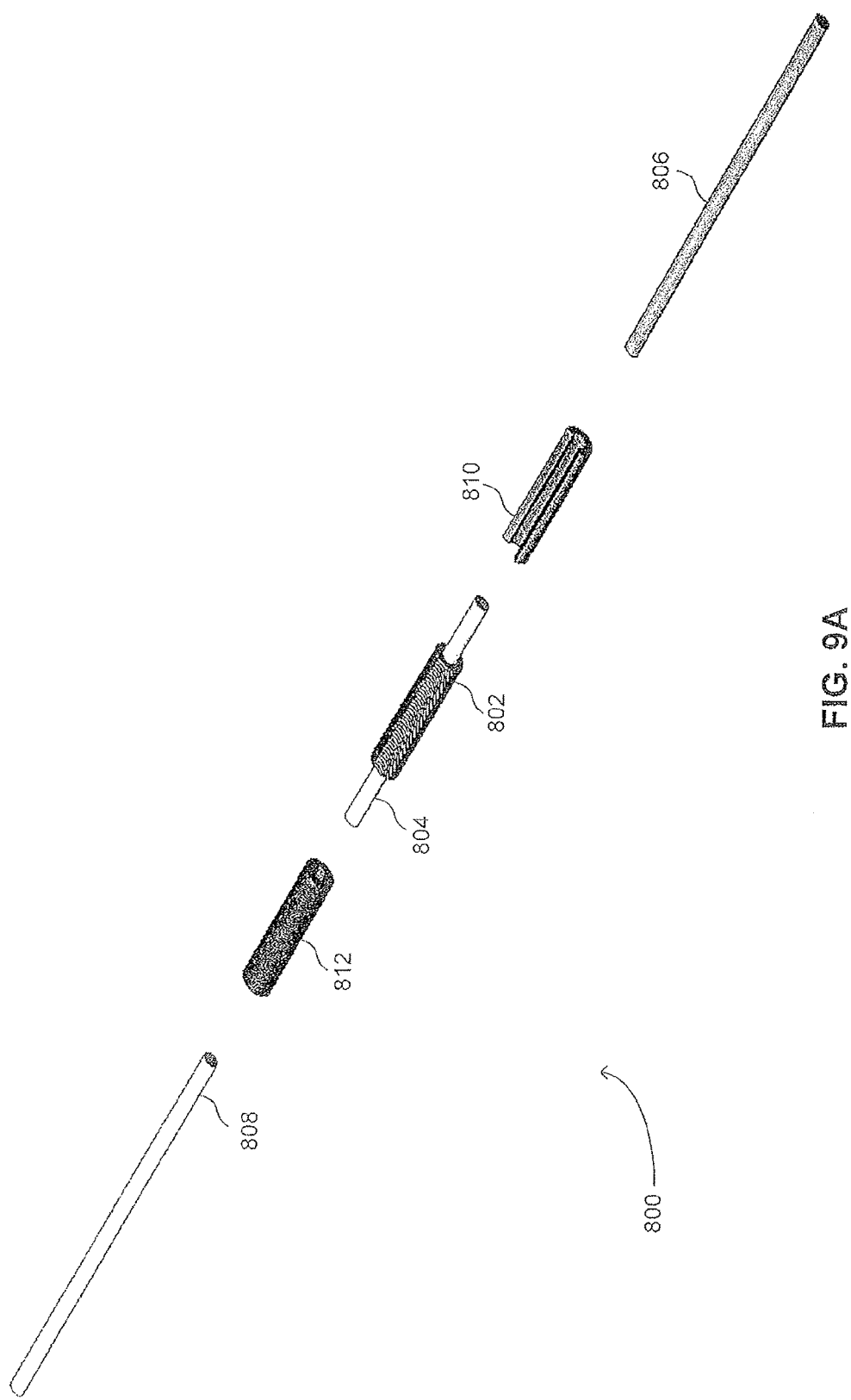

SENSOR MOUNTED FLEXIBLE GUIDEWIRE

CROSS-REFERENCE TO RELATED APPLICATIONS

This application is a continuation of U.S. patent application Ser. No. 12/357,971 ("the 971 application"), filed Jan. 22, 2009, now pending, which claims the benefit of U.S. provisional patent application No. 61/028,665 ("the '665 application"), filed Feb. 14, 2008, and of U.S. provisional patent application No. 61/023,007 ("the '007 application"), filed Jan. 23, 2008. The '971 application, the '665 application, and the '007 application are hereby incorporated by reference in their entireties as though fully set forth herein.

BACKGROUND a. Field of the Disclosed Technique

The disclosed technique relates to guidewires, in general, and to methods and systems for including electronic components in guidewires and for making guidewires more flexible, in particular.

b. Background of the Disclosed Technique

Guidewires are employed in noninvasive operations, to enable the physician to navigate to a desired location within the lumen of the body of the patient, and then insert the catheter to the desired location, with the aid of the guidewire. Such guidewires are known in the art. One type of guidewire includes a sensor at the tip thereof, which is connected to an electronic unit, with a pair of wires which pass through a lumen within the guidewire. The guidewire includes a coil in front of the sensor, to enable maneuverability. Another type of guidewire includes a sensor at the tip thereof, which is connected to the electronic unit, with a pair of wires, which pass through the lumen within the guidewire. This guidewire is devoid of a flexible element to provide maneuverability.

U.S. Pat. No. Re. 35,648 issued to Tenerz et al., and entitled "Sensor Guide Construction and Use Thereof," is directed to a guidewire which includes a thin outer tube, an arched tip, a radiopaque coil, a solid metal wire, a sensor element, and a signal transmitting cable. The radiopaque coil is welded to the arched tip. The solid metal wire is formed like a thin conical tip, and it is located within the arched tip and the radiopaque coil. The solid metal wire successively tapers toward the arched tip. At the point where the solid metal wire joins the radiopaque coil, the thin outer tube commences. The signal transmitting cable extends from the sensor element to an electronic unit, through an air channel within the thin outer tube.

U.S. Pat. No. 4,873,986 issued to Wallace, and entitled "Disposable Apparatus for Monitoring Intrauterine Pressure and Fetal Heart Rate," is directed to an apparatus to monitor the fetal condition during labor and childbirth. The apparatus includes a cable, a pressure transducer, a plug, and a pair of wires. The pressure transducer is located within the leading edge of the cable. The plug is located at a proximal end of the cable. The signals from the pressure transducer are conveyed to the plug, by way of the pair of wires, which pass through a vent channel within the cable.

U.S. Pat. No. 6,428,489 issued to Jacobsen et al and entitled "Guidewire System," is directed to a catheter guidewire which includes an elongate solid body. Around this elongated solid body about, a catheter guided toward a target location in the vasculature system of a body. The elongate body includes a proximal end and a distal end, with the distal end being curved. Cuts are formed by either saw-cutting, laser cutting or etching at spaced-apart locations along the length of the body thereby increasing the lateral flexibility of the guidewire. Integral beams are also formed within the body to maintain its torsional strength. The relative location and size of cuts and beams may be selectively adjusted thereby determining the direction and degree of flexure, and the change in torsional stiffness relative to flexibility.

SUMMARY OF THE PRESENT DISCLOSED TECHNIQUE

It is an object of the disclosed technique to provide a novel flexible guidewire.

In accordance with the disclosed technique, there is thus provided a flexible guidewire including a hollow tube, a plug and a tubular spring. The hollow tube has a proximal section and a distal section. The distal section has a distal tip. The outer diameter of the distal section gradually decreases toward the distal tip. The outer diameter of the distal tip is larger than the smallest outer. diameter of the distal section. The spring is place around the distal section of the hollow tube for maintaining the outer diameter of the hollow tube over the length thereof and for supporting compressive loads. The plug is coupled with the distal tip of the hollow tube, for creating a non-traumatic tip.

In accordance with another aspect of the disclosed technique, there is thus provided a method for forming a flexible guidewire. The method comprises the procedures of reducing the outer diameter of the distal section of a hollow tube and placing a tubular spring over the distal section of the hollow tube. The method further comprises the procedures of enlarging the distal end of the distal tip of the hollow tube, thereby creating a sensor housing, and inserting a plug onto the sensor housing.

In accordance with a further aspect of the disclosed technique, there is thus provided a flexible guidewire including a grooved corewire, a plug and a tubular spring. The grooved corewire has a proximal section and a distal section. The distal section has a distal tip. The outer diameter of the distal section gradually decreases toward the distal tip. The grooved corewire has a groove engraved along the length thereof. The spring is place around the distal section of the hollow tube for maintaining the outer diameter of the hollow tube over the length thereof and for supporting compressive loads. The plug is coupled with the distal tip of the grooved corewire, for creating a non-traumatic tip.

In accordance with another aspect of the disclosed technique, there is thus provided a flexible guidewire including a flexible corewire, a sensor core for coupling a sensor therewith and a coupler. The sensor core exhibits a diameter substantially similar to the diameter of the flexible corewire. The sensor covers one portion of said sensor core. The other portion of the sensor core extends from at least one side of the sensor. The coupler exhibits the shape of a hollow tube with a part of the wall of said hollow tube removed along the length of the hollow tube. The inner diameter of the hollow tube is substantially similar to the diameters of the corewire and the sensor core.

BRIEF DESCRIPTION OF THE DRAWINGS

The disclosed technique will be understood and appreciated more fully from the following detailed description taken in conjunction with the drawings in which:

FIG. 9A is a schematic perspective exploded illustrations of a guidewire constructed and operative in accordance with a further embodiment of the disclosed technique.

DETAILED DESCRIPTION OF THE EMBODIMENTS

The disclosed technique overcomes the disadvantages of the prior art by providing a novel guidewire design and forming technique. The novel design enables electronic components, such as sensors and electrical wires, to be placed within the guidewire, in particular in the tip of the guidewire. Such electronic components allow for scalar and vector values to be measured at the guidewire's tip. The design also increases the flexibility of the guidewire, in particular at its distal end. The novel forming technique enables a guidewire to be formed having a substantially increased level of flexibility over prior art guidewires. Throughout the description, the guidewire of the disclosed technique is described in reference to medical guidewires. It is noted that the terms "position" and "location" are used interchangeably throughout the description and in general refer to the three dimension location of an object in a predefined coordinate system.

Figure 1A:
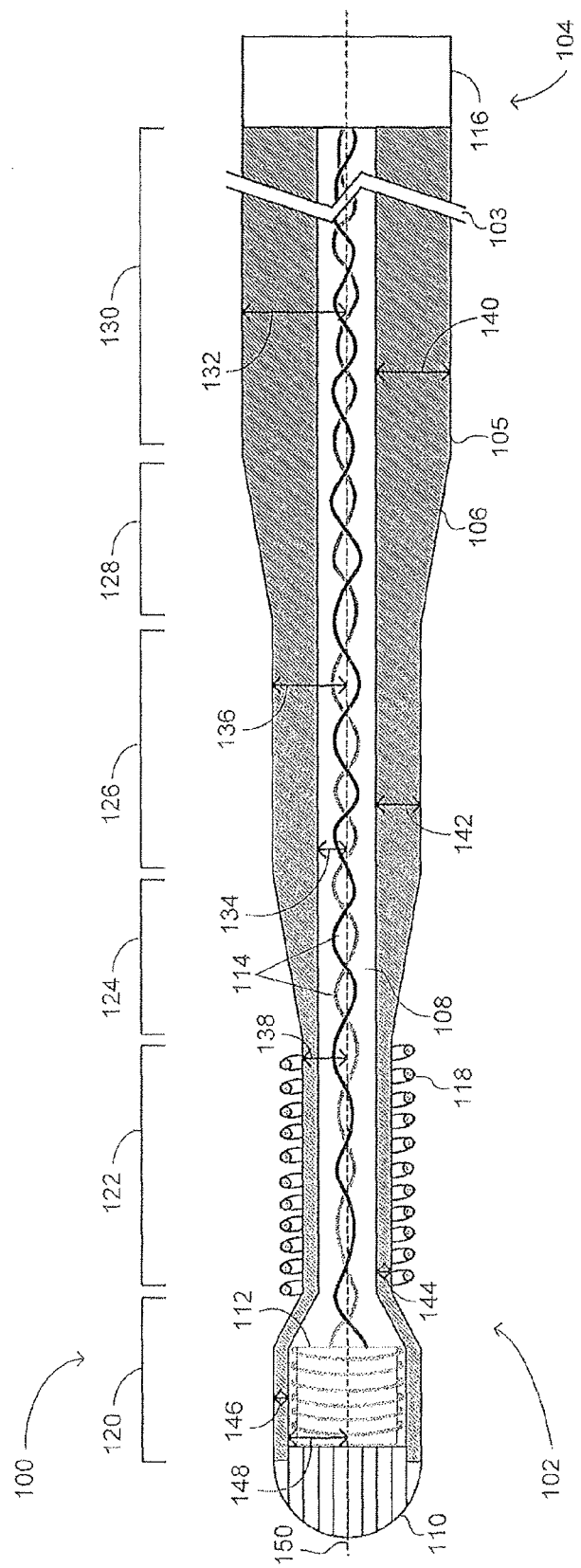
FIG. 1A is a schematic illustration of a guidewire in a cross-sectional view, constructed and operative in accordance with an embodiment of the disclosed technique.

Reference is now made to FIG. 1A, which is a schematic illustration of a guidewire, in a cross-sectional view, generally referenced 100, constructed and operative in accordance with an embodiment of the disclosed technique. FIG. 1A substantially shows the inside of guidewire 100. Guidewire 100 includes a hollow tube 105, a plug 110, a sensor 112, a twisted pair of wires 114 and a tubular spring 118. Guidewire 100 can be coupled with an interconnect 116. In general, guidewire 100 includes two sections, a distal section 102 and a proximal section 104. Distal section 102 refers to the distal end of guidewire 100, the end of guidewire 100 which is distant from interconnect 116. Proximal section 104 refers to the proximal end of guidewire 100, the end of guidewire 100 which is nearest to interconnect 116. In FIG. 1A, distal section 102 and proximal section 104 are separated by a set of lines 103. Hollow tube 105 includes a walled section 106 and a hollow section 108. Hollow section 108 can also be referred to as a cavity or a lumen. Twisted pair of wires 114, referred to herein as twisted, pair 114, are coupled with sensor 112 and with interconnect 116. Plug 110 is coupled with the distal tip of guidewire 100. As explained in further detail below, tubular spring 118 is placed around a particular section of distal section 102 of guidewire 100. Sensor 112 and twisted pair of wires 114 are located inside hollow tube 105 in hollow section 108.

Sensor 112 is sensor capable of measuring scalar values such as pressure and temperature as well as vector values such as position and orientation of a magnetic field. For example, sensor 112 is a coil sensor capable of measuring the strength and orientation of a magnetic field. In general, micro-coil sensor can have a thickness on the order of a few hundred micrometers, such as 250 μm. Twisted pair 114 includes wires capable of transferring electrical signals from sensor 112 to interconnect 116. The wires of twisted pair 114 can have a thickness on the order of tens of micrometers, for example, between 10-25 μm. Plug 110 can be made of metal or of a polymer bonded into guidewire 100. Plug 110 may further be made of bonding material shaped into a hemispherical shape. Plug 110 is coupled to the distal tip of guidewire 100 by gluing, bonding, welding or soldering. Plug 110 can also just be glue. Tubular spring 118 is a tube exhibiting lateral flexibility (i.e., perpendicular to the central axis of the tube). Tubular spring 118 is, for example, a metal (e.g., Stainless Steel, Platinum, Iridium, Nitinol) coil spring a flexible polymer tube or a braided or coiled plastic tube. Tubular spring 118 maintains the outer diameter of guidewire 100 over the length 25 thereof (i.e., typically tubular spring 118 maintains diameter 132). Furthermore, tubular spring supports compressive loads and resists buckling of the section 122 without substantially increasing torsional and bending stiffness. Tubular spring 118 can also be made of a radiopaque material, which prevents radiation from passing there through. Interconnect 116 enables guidewire 100, and in particular twisted pair of wires 114, to be coupled with other devices, such as a computer, a power source, a device measuring magnetic field strength and orientation and the like. Guidewire 100 may be further covered by a thin elastic polymer layer (not shown) over sections 120 and 122. This polymer layer is typically a heat shrink tube of a few microns thickness, which provides a slick, smooth and lubricious surface.

As mentioned above, guidewire 100 can be used to measure various scalar and vector values and in particular scalar and vector values as detected and determined at the distal tip of guidewire 100. When sensor 112 is a micro-coil sensor, sensor 112 and located in the distal tip of guidewire 100 guidewire 100 can be used to determine the strength and orientation of a magnetic field at the distal tip of guidewire 100, which in turn can be used to determine the position and orientation of the distal tip of guidewire 100. For example, if guidewire 100 is used in a medical application, where guidewire 100 is inserted inside a living object, such as a human or an animal, then guidewire 100 can determine the position and orientation of its distal tip based on the measurements of sensor 112. In general, in such an application a magnetic field is generated in the vicinity of the living object and sensor 112 is capable of measuring the magnetic field strength and orientation. These measurements are provided as electrical signals from sensor 112 to twisted pair 114 which in turn provide the electrical signals to interconnect 116. Interconnect 116 can be coupled with a computer capable of determining the position and orientation of the micro-coil sensor based on the electrical signals received. Since sensor 112 is located in the distal tip of guidewire 100, the position and orientation of sensor 112 is substantially the position and orientation of the distal tip of guidewire 100.

In position sensing applications involving magnetic fields, magnetic interference, such as induced electrical currents, can cause errors and biases in the electrical signals provided from twisted pair 114 to interconnect 116. In order to reduce the amount of magnetic interference, the wires located inside hollow section 108 are generally twisted, which reduces the amount of induced electrical current in the wires due to the presence of a magnetic field. Furthermore, tubular spring 118 may be made of a radiopaque material such that it can be seen on an X-ray. If guidewire 100 is used in a medical application where it is inserted inside a living object, and tubular spring 118 is made of a radiopaque material, then, tubular spring 118 will appear on an X-ray of the living object and therefore, distal section 102 of the guidewire will also appear on the X-ray image. This information can be used along with the measurements of sensor 112 to enhance the determination of the position and orientation of the distal tip of guidewire 100.

Figure 1B:
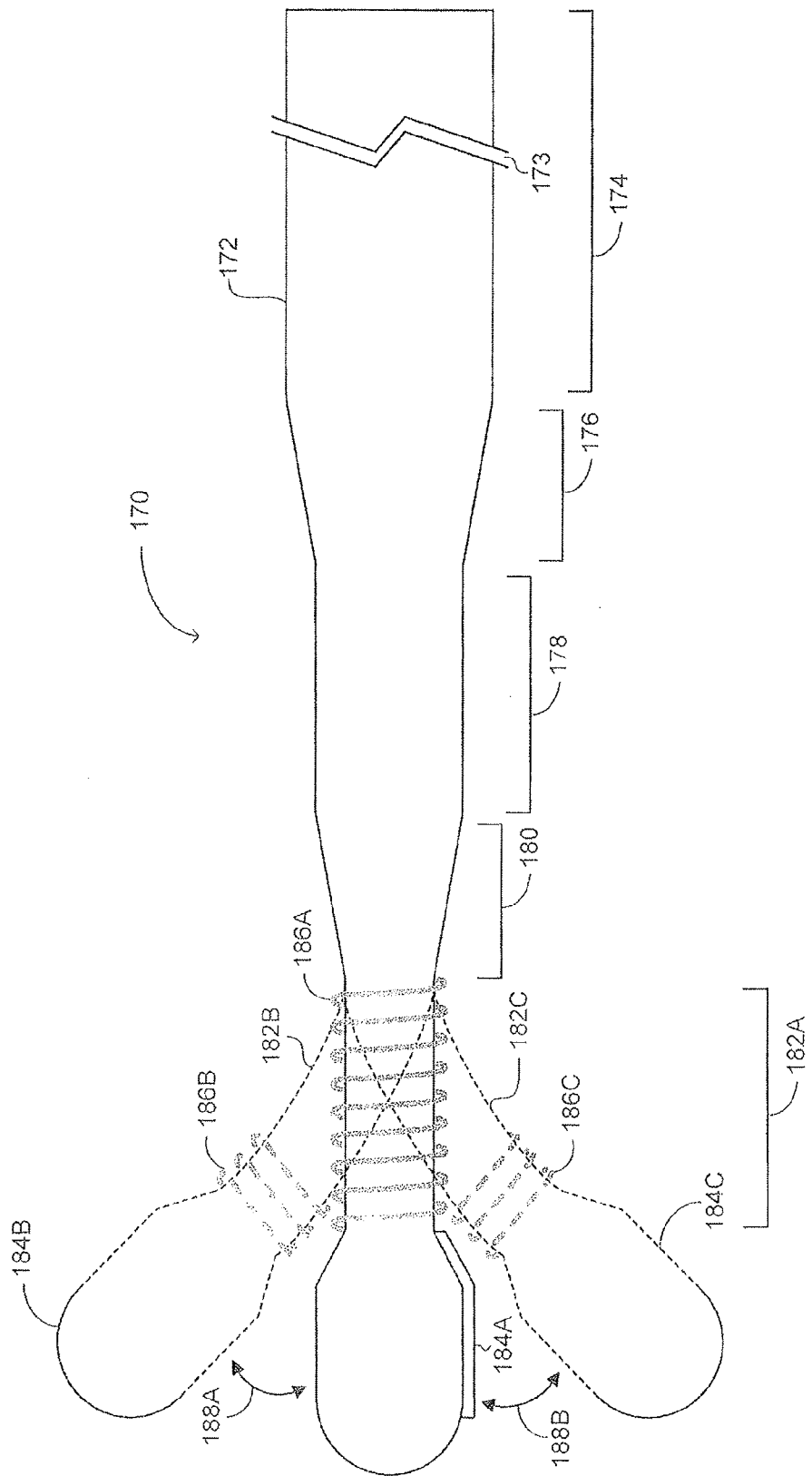
FIG. 1B is a schematic illustration showing the flexibility of a guidewire, constructed and operative in accordance with another embodiment of the disclosed technique.

As described in more detail in FIG. 1B, distal section 102 of guidewire 100 is flexible which provides increased maneuverability to guidewire 100. Increased maneuverability enables a user of guidewire 100 to more easily maneuver the guidewire when it is inserted into a living object. The flexibility of the distal end of guidewire 100 is achieved by changing the outer diameter of walled section 106 of hollow tube 105 as, further described. In general, to increase the flexibility of hollow tube 105, it is required to reduce the outer diameter thereof, while maintaining the ability of hollow tube 105 to withstand compressive loads, buckling and kinking Hollow tube 105 is generally made of a metal, such as Stainless Steel or Nitinol. In the embodiment shown in FIG. 1A, hollow tube 105 is made from a single piece of metal. The fact that hollow tube 105 is made of metal provides twisted pair 114 with shielding from electromagnetic interferences. Thus, twisted pair 114 may be an unshielded twisted pair, thereby reducing the thickness of twisted pair 114 to the order of tens of micrometers. Hollow tube 105 can be defined by the diameter of hollow section 108, known as the inner diameter, as well by the diameter of walled section 106, known as the outer diameter. In FIG. 1A, both the inner and outer diameters of hollow tube 105 are measured from a centerline 150. The inner diameter, as shown by an arrow 134, is substantially on the order of hundreds of micrometers, such as 100 μm. In cardio-logical applications, the inner diameter, shown by an arrow 134, is substantially on the order of tens of micrometers. As can be seen in FIG. 1A, the inner diameter of hollow tube 105 does not change along the length of guidewire 100. The outer diameter, as can be seen in FIG. 1A, changes along the length of guidewire 100, as shown by an arrow 132, an arrow 136 and an arrow 138. Hollow tube 105 can also be described in terms of the thickness of walled section 106. For example, as the outer diameter of hollow tube 105 reduces, the thickness of walled section 106 also reduces, as shown by an arrow 140, an arrow 142 and an arrow 144. The outer diameter shown by arrow 132 represents the original diameter of hollow tube 105, which is substantially on the order of hundreds of micrometers, such as 350 μm. In general, the outer diameter of distal section 102 of guidewire 100 is reduced, in a step-like, gradual manner, using various techniques such as grinding and drawing.

As can be seen in FIG. 1A, a first section 130 represents the shape of hollow tube 105 over a majority of the length of guidewire 100. Recall that lines 103 represent a break between the distal and proximal sections of guidewire 100 wherein the dimensions of the guidewire do not change and remain fixed. Guidewire 100 can measure, for example up to 200 centimeters. Section 130 can measure, for example, up to 160 centimeters. Adjacent to first section 130 is a first transition section 128, where the outer diameter of walled section 106 is gradually tapered until a first predetermined reduced outer diameter, such as the outer diameter defined by arrow 136. Adjacent to first transition section 128 is a second section 126, where the dimensions of the guidewire do not change and remain fixed. Adjacent to second section 126 is a second transition section 124, where the outer diameter of walled section 106 is gradually tapered until a second predetermined reduced outer diameter, such as the outer diameter defined by arrow 138. Adjacent to second transition section 124 is a third section, which is subdivided into a floppy section 122 and a sensor housing section 120. This third section is characterized in that the thickness of walled section 106 does not change and remains fixed as can be seen from arrow 144 and an arrow 146, both of which are the same size. In general, the length of the distal section, over which the diameter of the guidewire is reduced (i.e., sections 120, 122, 124, 126 and 128) is between 20-40 centimeters.

In general, the thickness of walled section 106 in the third section is substantially on the order of tens of micrometers, such as 25 μm, meaning that the outer diameter in floppy section 122, as shown by an arrow 138, is substantially on the order of hundreds of micrometers, such as 125 μm. At an outer diameter of hundreds of micrometers, floppy section 122 and sensor housing section 120 of guidewire 100 have increased flexibility and maneuverability. In general, floppy section 122 can typically measure between 40 mm to 300 mm. As floppy section 122 is flexible and not rigid, tubular spring 118 is placed around this section to strengthen the distal tip of guidewire 100 while at the same time not reducing its flexibility. Sensor housing section 120, which initially had an inner diameter similar to the inner diameter of floppy section 122, as shown by arrow 134, is enlarged to an inner diameter as shown by an arrow 148 such that sensor 112 can be inserted into sensor housing section 120. When sensor 112 is a micro-coil sensor, the thickness of sensor 112 may be on the order of hundreds of micrometers, such as 250 μm, meaning that the inner diameter of the distal tip of guidewire 100, in this example, is substantially doubled, from approximately 100 μm to 200 μm. The outer diameter of sensor housing section 120 can be increased by drawing the distal tip of guidewire 100 over a mandrel. In general, sensor housing section 120 can typically measure between 1 mm and 5 mm. It is noted that the dimensions of the general configuration, as shown in FIG. 1A, can be changed and varied so as to provide increased flexibility, pushability, torque response and tactile feel. For example, more transitions sections or fewer transition sections could have been present in guidewire 100. The number of transition sections, as well as their respective lengths can be determined and altered by one skilled in the art according to the needs of a particular application, user or both. Alternatively, the outer diameter of guidewire 100 may decrease continuously, either linearly or according to a determined function (e.g., the outer diameter may decrease exponentially).

Reference is now made to FIG. 1B, which is a schematic illustration showing the flexibility of a guidewire, generally referenced 170, constructed and operative in accordance with another embodiment of the disclosed technique. Guidewire 170 is substantially similar to guidewire 100 (FIG. 1A). Guidewire 170 is constructed from a hollow tube 172. As in FIG. 1A, the distal and proximal sections of guidewire 170 are separated by a set of lines 173. As in FIG. 1A, hollow tube 172 is characterized by an outer diameter and an inner diameter, whereby the outer diameter of the hollow tube is reduced at the distal end of the guidewire. Guidewire 170 includes a first section 174, which represents the shape of hollow tube 172 over a majority of the length of guidewire 170. In first section 174, the dimensions of the guidewire do not change and remain fixed. Adjacent to first section 174 is a first transition section 176, where the outer diameter of hollow tube 172 is gradually tapered until a first predetermined reduced outer diameter. Adjacent to first transition section 176 is a second section 178, where the dimensions of the guidewire do not change and remain fixed. Adjacent to second section 178 is a second transition section 180, where the outer diameter of hollow tube 172 is gradually tapered until a second predetermined reduced outer diameter. Adjacent to second transition section 172 is a third section, which is subdivided into a floppy section 182A and a sensor housing section 184A. This third section is characterized in that the thickness of the walled section of hollow tube 172 (not shown) does not change and remains fixed.

In FIG. 1B, a tubular spring 186A is placed around floppy section 182A in order to strengthen the third section while also maintaining the flexibility of this section. Two additional positions of the floppy section and the sensor housing section of guidewire 170 are shown using broken lines, demonstrating the flexible nature of the third section. In a first additional position, shown by a floppy section 182B, a sensor housing section 184B and a tubular spring 186B, the distal end of guidewire 170 is displaced by an amount shown as an arrow 188A. In a second additional position, shown by a floppy section 182C, a sensor housing section 184C and a tubular spring 186C, the distal end of guidewire 170 is displaced by an amount shown as an arrow 188B. Due to the reduced outer diameter of the floppy section and the sensor housing section of guidewire 170, the two additional positions shown in FIG. 1B are possible. Also, because the tubular spring applies a restoring force when the distal end of guidewire 170 is in either of the two additional positions shown in FIG. 1B, the distal end of guidewire 170 maintains a certain amount of rigidity as the tubular spring is always trying to maintain the floppy section in the position of floppy section 182A.

Figure 2:
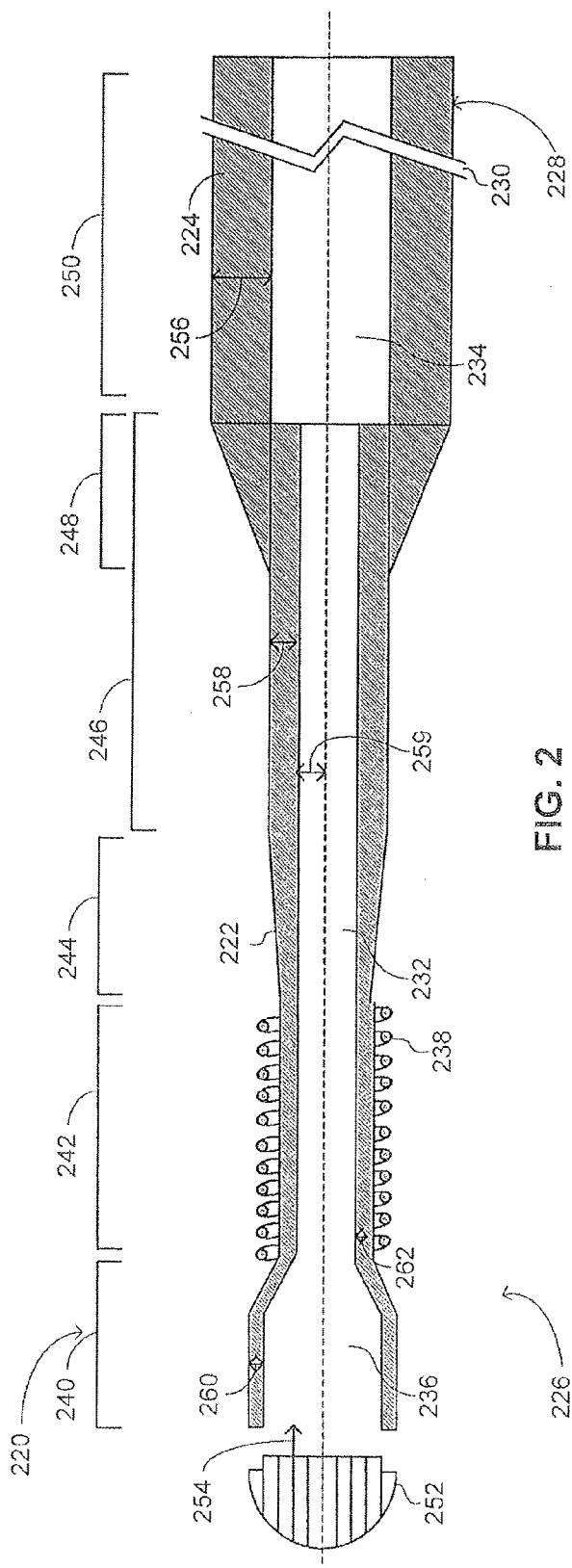
FIG. 2 is a schematic illustration of another guidewire, in a cross-sectional view, constructed and operative in accordance with a further embodiment of the disclosed technique.

Reference is now made to FIG. 2, which is a schematic illustration of another guidewire, in a cross-sectional view, generally referenced 220, constructed and operative in accordance with a further embodiment of the disclosed technique. Guidewire 220 is substantially similar to guidewire 100 (FIG. 1A) and includes a distal section 226, a proximal section 228 and a set of lines 230 separating the two. Unlike the embodiment of the guidewire shown in FIG. 1A, guidewire 220 is constructed from two hollow tubes of different inner and outer diameters, a thicker hollow tube 224 and a thinner hollow tube 222. Thicker hollow tube 224 and thinner hollow tube 222 can both be hypotubes. In general, thinner hollow tube 222 is shorter in length than thicker hollow tube 224. For example, thinner hollow tube 222 may typically measure between 5 and 30 centimeters, whereas thicker hollow tube 224 may typically measure between 160 and 170 centimeters. As in FIG. 1A, guidewire 220 includes a tubular spring 238 and a plug 252, which is placed over the distal end of guidewire 220 in the direction of an arrow 254. Guidewire 220 has a lumen 236, where a sensor (not shown) can be placed, and a hollow section 232, where a twisted pair of wires (not shown) can be placed, which are coupled with the sensor. Guidewire 220 can also be coupled with an interconnect (not shown). Similar to guidewire 100 (FIG. 1A), guidewire 220 may be also be covered by a thin elastic polymer layer (not shown) over sections 240 and 242.

As in FIG. 1A, guidewire 220 has an initial outer diameter which is tapered in distal section 226 to enable the distal section of guidewire 220 to have increased flexibility. As shown in FIG. 2, guidewire 220 includes a first section 250, which represents the shape of thicker hollow tube 224 over a majority of the length of guidewire 220. In first section 250, the dimensions of the guidewire do not change and remain fixed. Adjacent to first section 250 is a first transition section 248, where the outer diameter of thicker hollow tube 224 is gradually tapered until a first predetermined reduced outer diameter. Adjacent to first transition section 248 and partially overlapping is a second section 246, where the dimensions of the guidewire do not change and remain fixed. The second section represents the initial shape of thinner hollow tube 222. Adjacent to second section 246 is a second transition section 244, where the outer diameter of thinner hollow tube 222 is gradually tapered until a second predetermined reduced outer diameter. Adjacent to second transition section 244 is a third section, which is subdivided into a floppy section 242 and a sensor housing section 240. This third section is characterized in that the thickness of the walled section of thinner hollow tube 222 does not change and remains fixed as shown by arrows 260 and 262.

In general, the outer and inner diameters of both thicker hollow tube 224 and thinner hollow tube 222 are on the order of hundreds of micrometers. For example, the inner and outer diameters of thicker hollow tube 224 may respectfully be 180 μm and 350 μm, whereas the inner and outer diameters of thinner hollow tube 222 may respectfully be 100 μm and 180 μm. The inner diameter of thinner hollow tube 222 is shown as an arrow 259. In general, the outer diameter of the thinner hollow tube is selected such that it is substantially similar to the inner diameter of the thicker hollow tube. In the embodiment shown in FIG. 2, thicker hollow tube 224 is coupled with thinner hollow tube 222 by either welding, bonding or gluing. As shown in FIG. 2, the area which is coupled between the two hollow tubes is where first transition section 248 and second section 246 overlap.

In this embodiment, the initial thickness of the walled section of each hollow tube, as shown by an arrow 256 and an arrow 258, is reduced and tapered by reducing the outer diameter of the walled section of each hollow tube. As mentioned above, the outer diameter can be reduced by grinding or drawing. In one embodiment, the outer diameters of thicker hollow tube 224 and thinner hollow tube 222 are both reduced after they have been coupled together. In another embodiment, the outer diameters of thicker hollow tube 224 and thinner hollow tube 222 are both reduced before they are coupled together. In a further embodiment, the outer diameters of thicker hollow tube 224 and thinner hollow tube 222 are both reduced before they are coupled together and after they are coupled together. It is noted that in this embodiment, sensor housing section 240 can be formed (i.e., the distal end of guidewire 220 can be enlarged) before tubular spring 238 is placed on floppy section 242. This can be achieved by first enlarging the distal end of guidewire 220 before thicker hollow tube 224 and thinner hollow tube 222 are coupled together. Once the distal end has been enlarged, tubular spring 238 can be placed over floppy section 242 and then thicker hollow tube 224 and thinner hollow tube 222 can be coupled together, thereby trapping tubular spring 238 between the larger outer diameters of sensor housing section 240 and first section 250. In another embodiment, the two hollow tubes can first be coupled together, then tubular spring 238 can be placed over floppy section 242 and finally, sensor housing section 240 can be enlarged to fit the sensor. As mentioned above in conjunction with FIG. 1A, the dimensions of the general configuration, as shown in FIG. 2, can be changed and varied so as to provide increased flexibility, pushability, torque response and tactile feel. For example, more transitions sections could have been present in guidewire 220. The number of transition sections, as well as their respective length can be determined and altered by one skilled in the art according to the needs of a particular application, user or both.

Figure 3A:
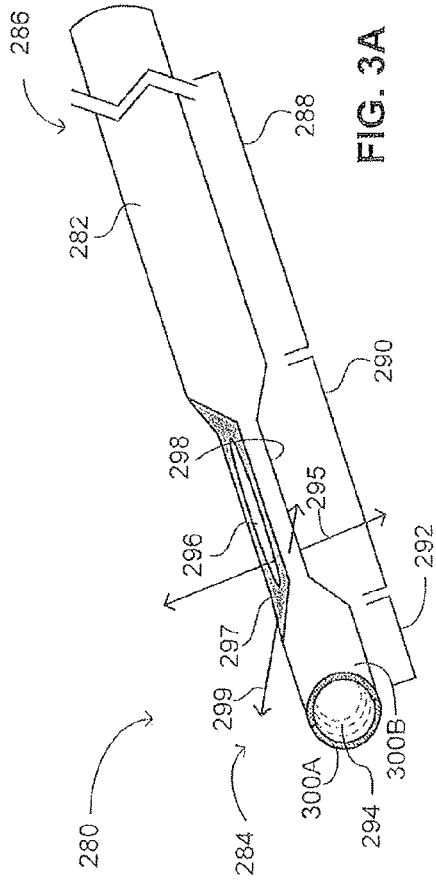
FIG. 3A is a perspective illustration of a guidewire having a tip which exhibits substantially increased flexibility, constructed and operative in accordance with another embodiment of the disclosed technique.

Reference is now made to FIG. 3A, which is a perspective illustration of a guidewire having a tip which exhibits substantially increased flexibility, generally referenced 280, constructed and operative in accordance with another embodiment of the disclosed technique. In general, the flexibility of the hollow tubes illustrated in FIGS. 1A and 2 are determined by the thickness of the walled section of each guidewire near the distal end, as shown by arrows 144 (FIG. 1A) and 146 (FIG. 1A) for guidewire 100 (FIG. 1A), and as shown by arrows 260 (FIG. 2) and 262 (FIG. 2) for guidewire 220 (FIG. 2). The flexibility is also determined by the inner diameter of each guidewire, as shown by arrow 134 (FIG. 1A) for guidewire 100 and by arrow 259 for guidewire 220. By reducing the thickness of the walled sections of these guidewires near, the distal end and by reducing the inner diameter, the flexibility of these guidewires can be increased. This flexibility is limited by two factors, the first being the minimal size of the inner diameter of each guidewire such that a twisted pair of wires can be threaded through. The second is the minimal thickness of the walled section of each guidewire such that the general form of the guidewire is maintained and that the walled section of each guidewire does not break or tear during use. In FIG. 3A, the distal end of guidewire 280 is formed, according to the disclosed technique, in a manner such that it exhibits increased flexibility over the flexibility of guidewires 100 and 220. Thus the distal tip of guidewire 280 exhibits substantial maneuverability.

Guidewire 280 is substantially similar to guidewire 100. Guidewire 280 has a distal section 284 and a proximal section 286. Guidewire 280 is constructed from a hollow tube 282. Guidewire 280 can be coupled with an interconnect (not shown). Also, guidewire 280 has a sensor (not shown) and a twisted pair of wires (not shown) threaded through the lumen (not shown) of hollow tube 282. The outer diameter of guidewire 280 is tapered in distal section 284 and the distal end of guidewire 280 is enlarged to enable the sensor to be placed therein. As in guidewire 100, the inner diameter of hollow tube 282 remains constant along the length of the guidewire. Guidewire 280 has a first section 288, where the outer diameter of the guidewire remains fixed and constant along a majority of the length of the guidewire. Adjacent to first section 288 is a floppy section 290, where the outer diameter of guidewire 280 is reduced to a predetermined reduced outer diameter and then kept constant at the predetermined reduced outer diameter. A tubular spring (not shown) can be placed around floppy section 290. Adjacent to floppy section 290 is a sensor housing section 292 where the sensor is placed. As can be seen in FIG. 3A, sensor housing section 292 is enlarged to enable the sensor to fit in. Similar to guidewire 100 (FIG. 1A), guidewire 280 may be also be covered by a thin elastic polymer layer (not shown) over sections 290 and 292.

In guidewire 280, a part of the walled section of hollow tube 282, in floppy section 290, is completely removed, thereby exposing the lumen of hollow tube 282. This is illustrated in FIG. 3A as an opening 296 and an opening 298. Openings 296 and 298 are located at opposite sides of hollow tube 282, thereby increasing the flexibility of guidewire 280 in a horizontal plane, as shown by an arrow 299. An area 297 represents the walled section of hollow tube 282 which is visible once a part of the walled section in floppy section 290 has been removed. The walled section removed in floppy section 290 can be removed by either grinding or cutting by laser. Besides removing a part of the walled section in floppy section 290, hollow tube 282 is split in two in a vertical plane, as shown by an arrow 295, from the beginning of sensor housing section 292 to substantially the end of floppy section 290. This splitting generates two distal ends (i.e., two prongs) in distal section 284, a distal end 300A and a distal end 300B. This is more clearly illustrated in FIG. 3B. It is noted that other embodiments of the construction of distal section 284 are possible. For example, instead of removing the upper and lower sides of the walled section of floppy section 290, the lateral sides of the walled section of floppy section 290 can be removed. In this embodiment, the sensor housing section and the floppy section would be split into two in a horizontal plane.

Once distal section 284 has been constructed as shown in FIG. 3A, the sensor is placed inside an opening 294, and the twisted wire pair, coupled with the sensor, are threaded through the lumen of hollow tube 282. Openings 296 and 298 may be filled with a glue to prevent the twisted pair of wires from moving and being exposed. However, when the glue affects the flexibility of distal section 284, glue may be applied only at selected locations along distal section 284 to prevent the twisted pair of wires from moving. Also distal ends 300A and 300B can be glued to the sensor to keep the sensor in place. A plug (not shown) can be placed over opening 294 to seal the sensor in. Similar to guidewire 100 (FIG. 1A), guidewire 320 may be also be covered by a thin elastic polymer layer (not shown) over sections 290 and 292.

Figure 3B:
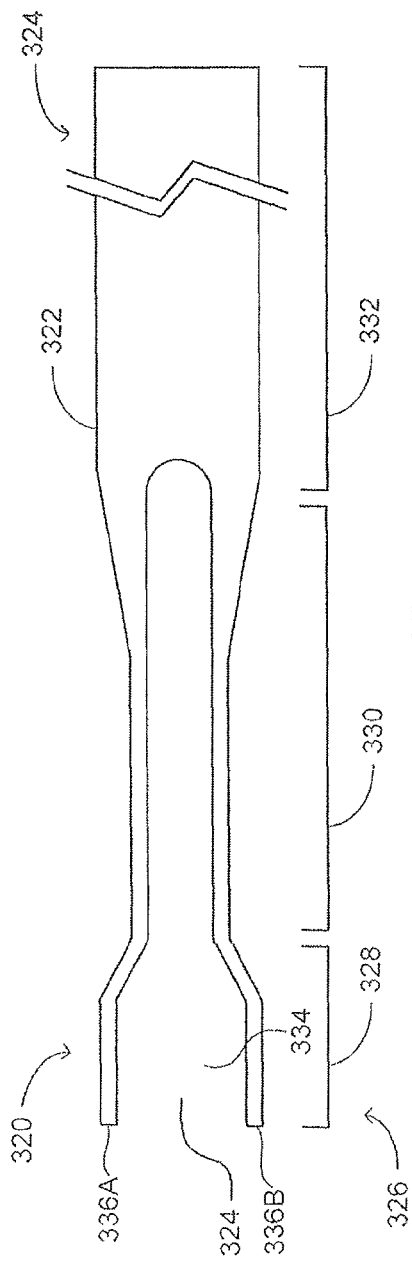
FIG. 3B is an orthographic illustration, in top view, of the guidewire of FIG. 3A, constructed and operative in accordance with a further embodiment of the disclosed technique.

Reference is now made to FIG. 3B, which is an orthographic illustration, in top view, of the guidewire of FIG. 3A, generally referenced 320, constructed and operative in accordance with a further embodiment of the disclosed technique. As can be seen in FIG. 3B, guidewire 320 is constructed from hollow tube 322, which is substantially similar to hollow tube 282 (FIG. 3A). Guidewire 320 has a proximal section 324 and a distal section 326 as well as a first section 332, a floppy section 330 and a sensor housing section 328. First section 332, floppy section 330 and sensor housing section 328 are respectively substantially similar to first section 288 (FIG. 3A), floppy section 290 (FIG. 3A) and sensor housing section 292 (FIG. 3A). As can be seen from the top view of FIG. 3B, sensor housing section 328 and floppy section 330 are split into two distal ends, a distal end 336A and a distal end 336B. A hollow 334 is where a sensor (not shown) is placed, in between distal end 336A and 336B.

Figure 3C:
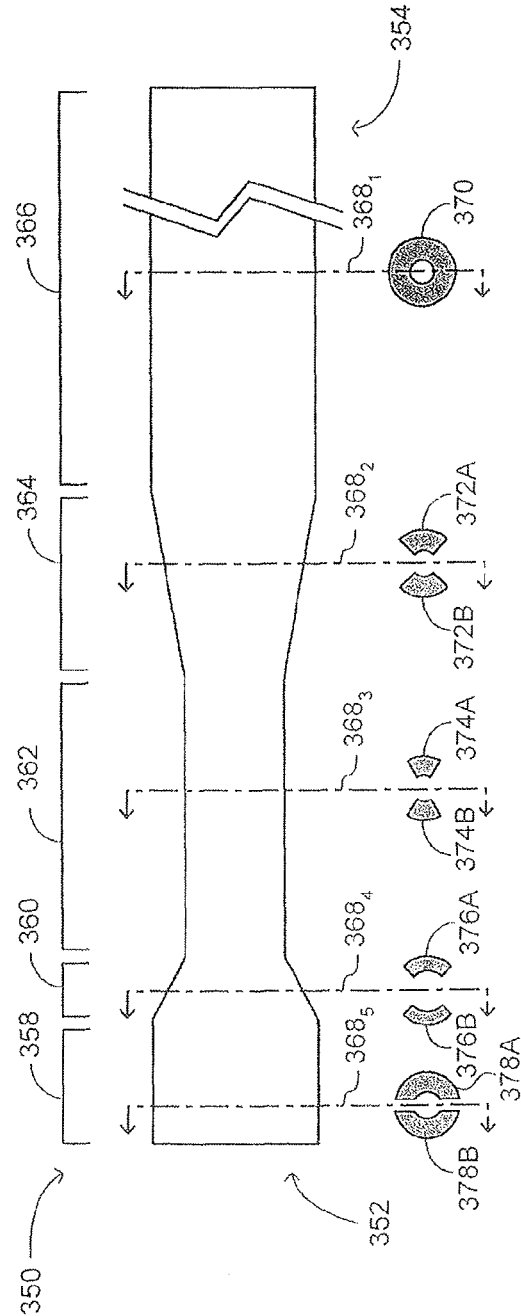
FIG. 3C is an orthographic illustration, in front view, of the guidewire of FIG. 3A, constructed and operative in accordance with another embodiment of the disclosed technique.

Reference is now made to FIG. 3C, which is an orthographic illustration, in front view, of the guidewire of FIG. 3A, also showing cross-sections of the guidewire, generally referenced 350, constructed and operative in accordance with another embodiment of the disclosed technique. As can be seen in FIG. 3C, guidewire 350 is substantially similar to guidewire 280. Guidewire 350 has a proximal section 354 and a distal section 356 as well as a first section 366, a first transition section 364, a floppy section 362, a second transition section 360 and a sensor housing section 358. First section 366, floppy section 362 and sensor housing section 358 are respectively substantially similar to first section 288 (FIG. 3A), floppy section 290 (FIG. 3A) and sensor housing section 292 (FIG. 3A). A first transition section and a second transition section are shown in both FIGS. 3A and 3B but are not specifically numbered.

In FIG. 3C, dash-dot lines $368_1$, $368_2$, $368_3$, $368_4$ and $368_5$ represent cut-away cross-sections of guidewire 350. In first section 366, a cross-section 370 shows that the hollow tube forming guidewire 350 has an initial outer diameter and is completely closed. In first transition section 364, the cross-sections 372A and 372B show that the outer diameter has been reduced and that the hollow tube of the guidewire is not completely closed and is split into two sections. As can be seen, the outer diameter of cross-sections 372A and 372B is smaller than the outer diameter of cross-section 370. It should be noted that in first transition section 364, a minority amount of the walled section of the hollow tube has been completely removed, as this represents the beginning of the area of guidewire 350 where the walled section of the hollow tube is removed. In floppy section 362, the cross-sections 374A and 374B show that the outer diameter has been further reduced from that of cross-sections 372A and 372B, and that the majority of the walled section of the hollow tube of the guidewire has been completely removed. In second transition section 360, the cross-sections 376A and 376B show that the outer diameter now remains constant, as the outer diameter of these cross-sections is substantially similar to the outer diameter as shown in cross-sections 374A and 374B. These cross-sections also show that only a minority of the walled section of the hollow tube of the guidewire has been completely removed, as this represents the end of the area of guidewire 350 where the walled section of the hollow tube is removed. In sensor housing section 358, the cross-sections 378A and 378B show that the outer diameter is still constant, as the outer diameter of these cross-sections is substantially similar to the outer diameter as shown in cross-sections 374A, 374B, 376A and 376B. Also, these cross-sections show that the hollow tube is cut in a vertical plane and split into two sections which are not coupled (i.e., two prongs).

Figure 4:
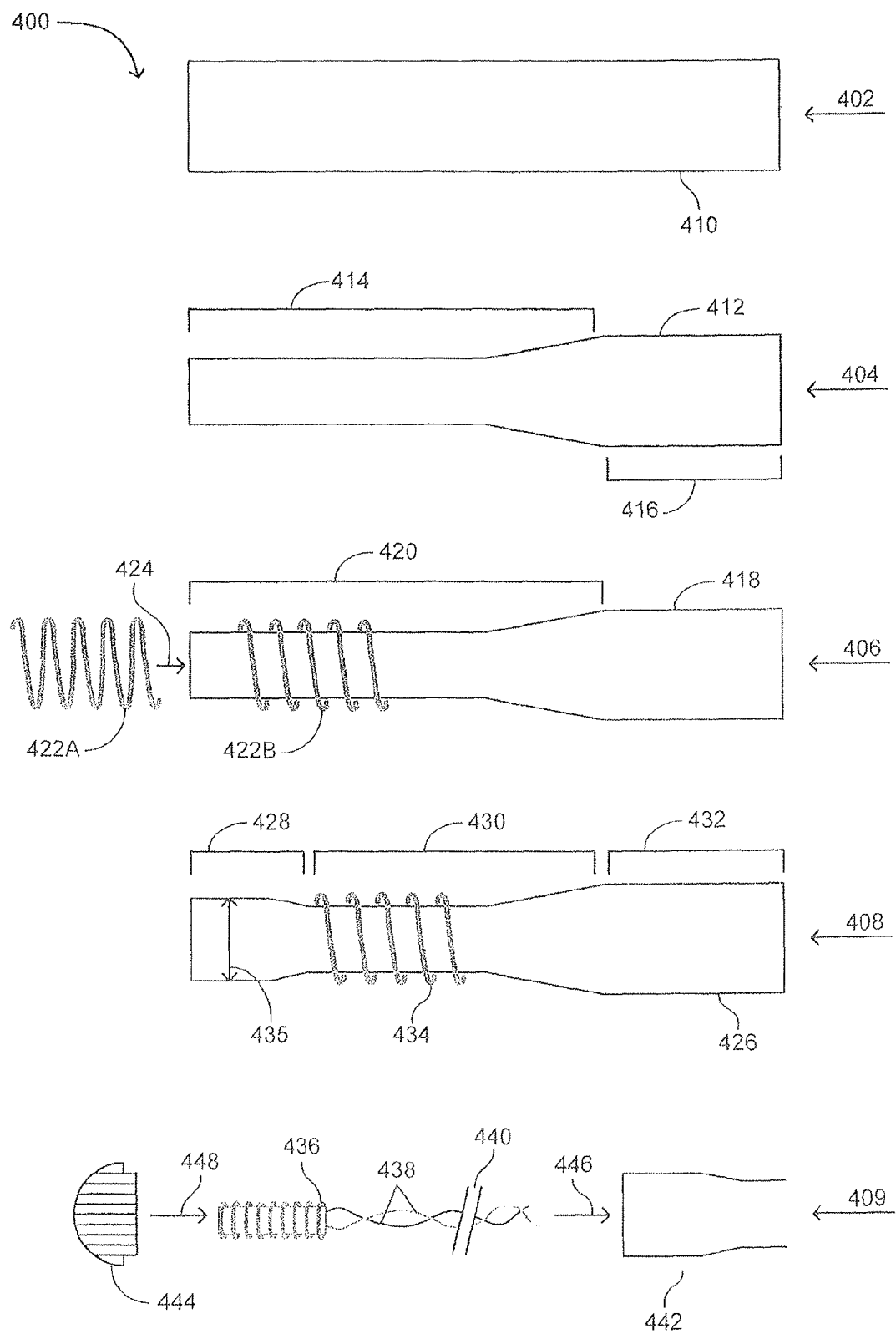
FIG. 4 is a schematic illustration showing the procedures executed in forming the guidewire of FIG. 3A, constructed and operative in accordance with a further embodiment of the disclosed technique.

Reference is now made to FIG. 4, which is a schematic illustration showing the procedures executed in forming the guidewire of FIG. 3A, generally referenced 400, constructed and operative in accordance with a further embodiment of the disclosed technique. In a first procedure 402, a hollow tube 410 having a fixed inner and outer diameter is selected. In a second procedure 404, the outer diameter of a distal section 414 of a hollow tube 412 is reduced in a step-like, gradual manner. The outer diameter of a proximal section 416 of hollow tube 412 remains constant. As mentioned above, the outer diameter can be reduced by grinding or by drawing. In procedure 404, a sub-section 415 of distal section 414 may be further grounded, or cut by a laser, to completely remove a part of the walled section of hollow tube 412 in sub-section 415, as shown as openings 296 and 298 (both in FIG. 3A) in FIG. 3A. Also, in procedure 404, distal section 414 is cut all the way through in a vertical plane, thereby generating two distal ends (not shown).

In a third procedure 406, once the outer diameter of a distal section 420 has been reduced and distal section 420 of a hollow tube 418 has been split into two, a tubular spring 422A such as a coil spring is placed over distal section 420 in the direction of an arrow 424. The tubular spring is placed over distal section 420 until it is in the location of a tubular spring 422B. In a fourth procedure 408, the distal end of a hollow tube 426 is enlarged, for example, by of drawing or pulling hollow tube 426 over a mandrel, or stamping the tip over a mandrel between two die sections thereby generating a sensor housing section 428. Section 428 may further be reinforced by a small section of thin tube placed there over there by holding the split section. A tubular spring 434 is essentially trapped in a floppy section 430, as the diameters of a first section 432 and sensor housing section 428 are larger than the diameter of tubular spring 434. The diameter of sensor housing section 428, as shown by an arrow which represents the full diameter of sensor housing section 428 and not the inner or outer diameter of that section, is large enough that a tubular spring (not shown) can be inserted. In a fifth procedure 409, once the general configuration of the guidewire has been prepared, a sensor coupled with a twisted pair of wires 438, referred herein as twisted pair 438, are threaded into the guidewire, in the direction of an arrow 446, through a sensor housing section 442. It is noted that twisted pair 438 may be long, as represented by set of lines 440. Once sensor 436 and twisted pair 438 are threaded through the guidewire, a plug 444 is inserted over the opening of sensor housing section 442 in the direction of an arrow 448. As mentioned above, a sensor 436 may be glued or bonded to the inner sides of sensor housing section 442. Also, the floppy section (not shown) of the guidewire may be covered with a glue to cover any section of twisted pair of wires 438 which are exposed. Twisted pair 438 can then be coupled with an interconnect, thereby generating a finished, functional guidewire, substantially similar in configuration to guidewire 280 (FIG. 3A) and in functionality to guidewire 100 (FIG. 1A). Additionally, an elastic polymer layer may be applied to the distal end of the guidewire. This elastic polymer layer is typically a heat shrink tube having a thickness in the order of a few microns, which provides a slick, smooth, lubricious surface.

Figure 5A:
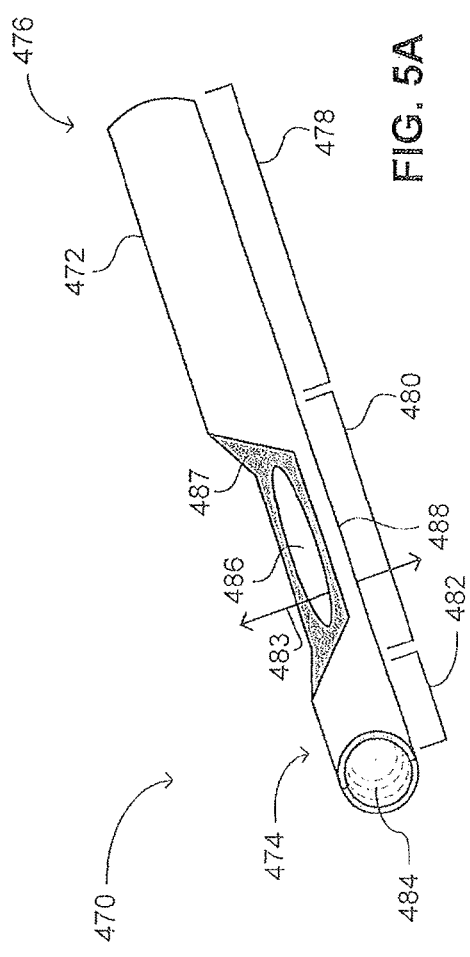
FIG. 5A is a perspective illustration of another guidewire having a substantially flexible tip, constructed and operative in accordance with another embodiment of the disclosed technique.

Reference is now made to FIG. 5A, which is a perspective illustration of another guidewire having a substantially flexible tip, generally referenced 470, constructed and operative in accordance with another embodiment of the disclosed technique. In FIG. 5A, the distal end of guidewire 470 is formed, according to the disclosed technique, in a manner such that it exhibits increased flexibility over the flexibility of guidewires 100 (FIG. 1A) and 220 (FIG. 2). Thus, the distal tip of guidewire 470 exhibits substantial flexibility, similar to the flexibility of guidewire 280 (FIG. 3A). Guidewire 470 is substantially similar to guidewire 100. Guidewire 470 has a distal section 474 and a proximal section 476. Guidewire 470 is constructed from a hollow tube 472. Guidewire 470 can be coupled with an interconnect (not shown). Also, guidewire 470 has a sensor (not shown) and a twisted pair of wires (not shown) threaded through the lumen (not shown) of hollow tube 472. The outer diameter of guidewire 470 is tapered in distal section 474 and the distal end of guidewire 470 is enlarged to enable the sensor to be placed therein. As in guidewire 100, the inner diameter of hollow tube 472 remains constant along the length of the guidewire. Guidewire 470 has a first section 478, where the outer diameter of the guidewire remains fixed and constant along a majority of the length of the guidewire. Adjacent to first section 478 is a floppy section 480, where the outer diameter of guidewire 470 is reduced to a predetermined reduced outer diameter and then kept constant at the predetermined reduced outer diameter. A tubular spring (not shown) can be placed around floppy section 480. Adjacent to floppy section 480 is a sensor housing section 482 where the sensor is placed. As can be seen in FIG. 5A, sensor housing section 482 is enlarged to enable the sensor to fit in. Similar to guidewire 100 (FIG. 1A), guidewire 470 may be also be covered by a thin elastic polymer layer (not shown) over sections 488 and 488.

In guidewire 470, a part of the walled section of hollow tube 472, in floppy section 480, is completely removed, thereby exposing the lumen of hollow tube 472. This is illustrated in FIG. 5A as an opening 486. As opposed to the configuration of guidewire 280 (FIG. 3A), guidewire 470 has an opening on only one side of hollow tube 472. Opening 486 is located on the upper side of hollow tube 472, thereby giving guidewire 470 an increase in flexibility in a vertical plane, as shown by an arrow 483. An area 487 represents the walled section of hollow tube 472 which is visible once a part of the walled section in floppy section 480 has been removed. The walled section removed in floppy section 480 can be removed by either grinding or cutting by laser. Unlike the configuration in FIG. 3A, floppy section 480 and sensor housing section 482 are not split into two separate ends. It is noted that other embodiments of the construction of distal section 474 are possible. For example, instead of removing the upper side of the walled section of floppy section 480, the lateral side or the lower side of the walled section of floppy section 480 can be removed. Once distal section 474 has been constructed as shown in FIG. 5A, the sensor is placed inside an opening 484, and the twisted pair of wires coupled with the sensor are threaded through the lumen of hollow tube 472. Opening 486 can be filled with a glue to prevent the twisted pair of wires from being exposed. A plug (not shown) can be placed over opening 484 to seal in the sensor.

Figure 5B:
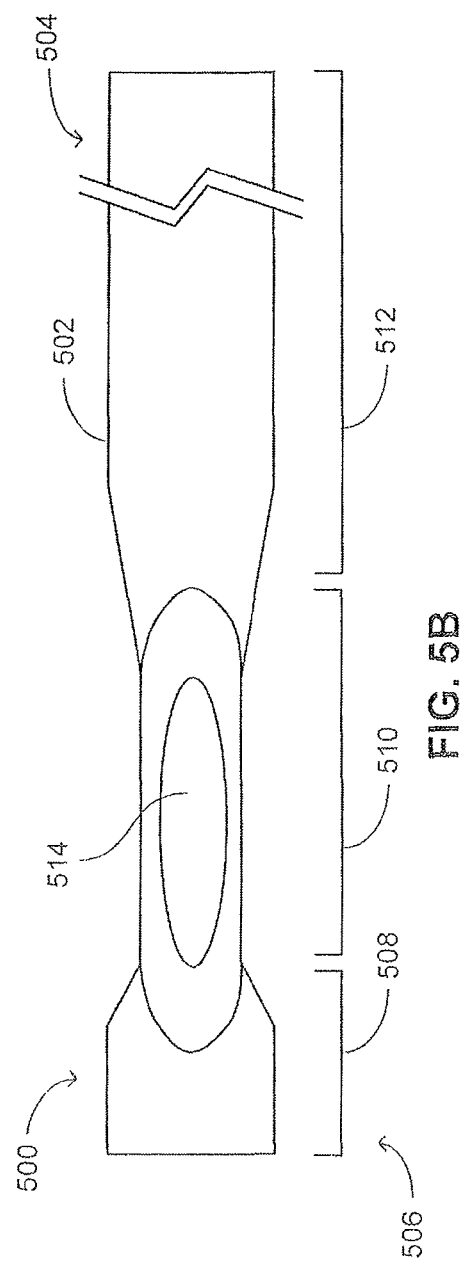
FIG. 5B is an orthographic illustration, in top view, of the guidewire of FIG. 5A, constructed and operative in accordance with a further embodiment of the disclosed technique.

Reference is now made to FIG. 5B, which is an orthographic illustration, in top view, of the guidewire of FIG. 5A, generally referenced 500, constructed and operative in accordance with a further embodiment of the disclosed technique. As can be seen in FIG. 5B, guidewire 500 is constructed from hollow tube 502, which is substantially similar to hollow tube 472 (FIG. 5A). Guidewire 500 has a proximal section 504 and a distal section 506 as well as a first section 512, a floppy section 510 and a sensor housing section 508. First section 512, floppy section 510 and sensor housing section 508 are respectively substantially similar to first section 478 (FIG. 5A), floppy section 480 (FIG. 5A) and sensor housing section 482 (FIG. 5A). As can be seen from the top view of FIG. 5B, a part of the walled section of floppy section 510 is completely removed. Unlike the guidewire shown in FIG. 3B, sensor housing section 508 is not split into two distal ends. Similar to guidewire 100 (FIG. 1A), guidewire 470 may be also be covered by a thin elastic polymer layer (not shown) over sections 508 and 510.

Figure 5C:
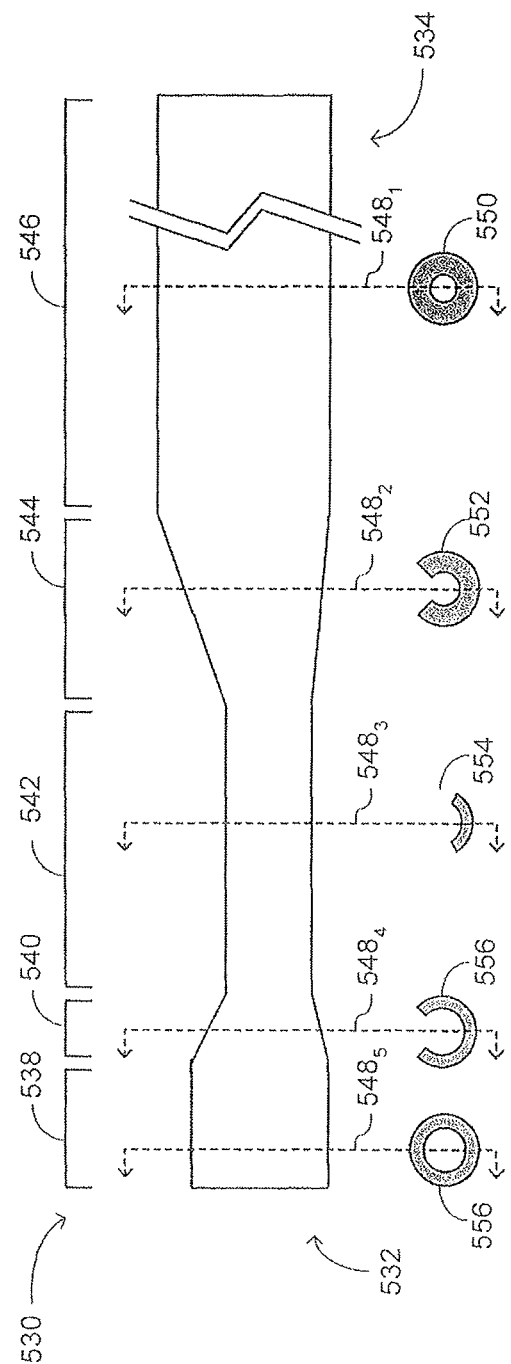
FIG. 5C is an orthographic illustration, in front view, of the guidewire of FIG. 5A, also showing cross-sections of the guidewire, constructed and operative in accordance with another embodiment of the disclosed technique.

Reference is now made to FIG. 5C, which is an orthographic illustration, in front view, of the guidewire of FIG. 5A, also showing cross-sections of the guidewire, generally referenced 530, constructed and operative in accordance with another embodiment of the disclosed technique. As can be seen in FIG. 5C, guidewire 530 is substantially similar to guidewire 470. Guidewire 530 has a proximal section 534 and a distal section 532 as well as a first section 546, a first transition section 544, a floppy section 542, a second transition section 540 and a sensor housing section 538. First section 546, floppy section 542 and sensor housing section 538 are respectively substantially similar to first section 478 (FIG. 5A), floppy section 480 (FIG. 5A) and sensor housing section 482 (FIG. 5A). A first transition section and a second transition section are shown in both FIGS. 5A and 5B but are not specifically numbered.

In FIG. 5C, dash-dot lines $548_1$, $548_2$, $548_3$, $548_4$ and $548_5$ represent cut-away cross-sections of guidewire 530. In first section 546, a cross-section 550 shows that the hollow tube forming guidewire 530 has an initial outer diameter and is completely closed. In first transition section 544, the cross-section 552 shows that the outer diameter has been reduced and that the hollow tube of the guidewire is not completely closed. As can be seen, the outer diameter of cross-section 552 is smaller than the outer diameter of cross-section 550. It should be noted that in first transition section 544, a minority amount of the walled section of the hollow tube has been completely removed, as this represents the beginning of the area of guidewire 530 where the walled section of the hollow tube is removed. In floppy section 542, the cross-section 554 shows that the outer diameter has been further reduced from that of cross-section 552, and that the majority of the walled section of the hollow tube of the guidewire has been completely removed thereby creating a single prong. In second transition section 540, the cross-section 556 shows that the outer diameter now remains constant, as the outer diameter of this cross-section is substantially similar to the outer diameter as shown in cross-section 554. This cross-section also show that only a minority of the walled section of the hollow tube of the guidewire has been completely removed, as this represents the end of the area of guidewire 530 where the walled section of the hollow tube is removed. In sensor housing section 538, the cross-section 558 shows that the outer diameter is still constant, as the outer diameter of this cross-section is substantially similar to the outer diameter as shown in cross-sections 556 and 554. Also, this cross-section shows that the hollow tube is completed, as in cross-section 550.

Figure 6:
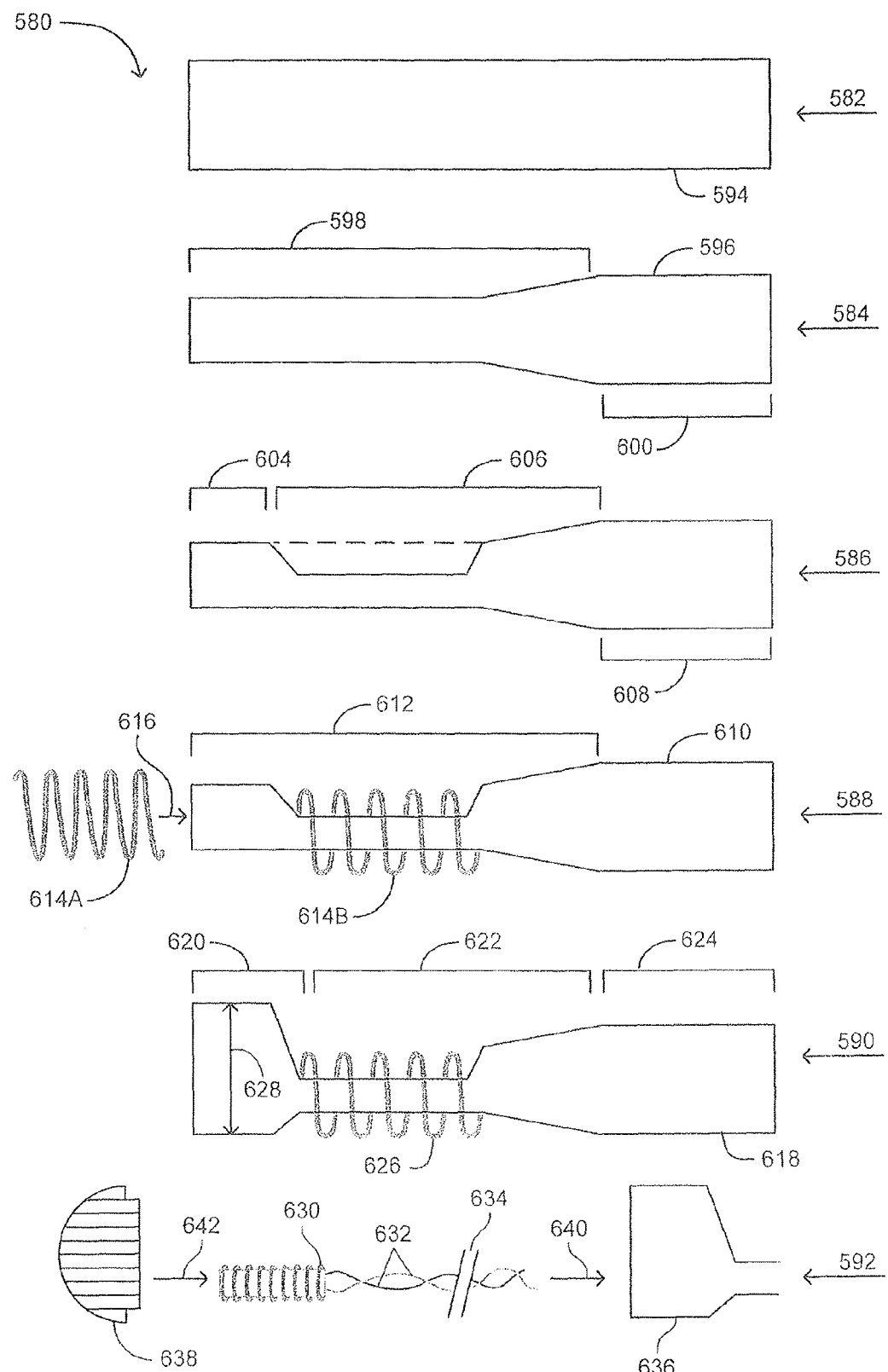
FIG. 6 is a schematic illustration showing the procedures executed in forming the guidewire of FIG. 5A, constructed and operative in accordance with a further embodiment of the disclosed technique.

Reference is now made to FIG. 6, which is a schematic illustration showing the procedures executed in forming the guidewire of FIG. 5A, generally referenced 580, constructed and operative in accordance with a further embodiment of the disclosed technique. In a first procedure 582, a hollow tube 594 having a fixed inner and outer diameter is selected. In a second procedure 584, the outer diameter of a distal section 598 of a hollow tube 596 is reduced in a step-like, gradual manner. The outer diameter of a proximal section 600 of hollow tube 596 remains constant. As mentioned above, the outer diameter can be reduced by grinding or by drawing. In a third procedure 586, a sub-section 606 of the distal section may be further grounded, or cut by a laser, to completely remove a part of the walled section of a hollow tube 602 in sub-section 606, as shown as opening 486 (FIG. 5A) in FIG. 5A. The area of the distal section cut out to generate sub-section 606 is shown as a dotted line in procedure 586. As can be seen, the diameter of sub-section 606 is smaller than the diameter of another sub-section 604.

In a fourth procedure 588, once the outer diameter of a distal section 612 has been reduced, a tubular spring 614A is placed over distal section 612 in the direction of an arrow 616. The tubular spring is placed over distal section 612 until it is in the location of a tubular spring 614B. In a fifth procedure 590, the distal end of a hollow tube 618, is enlarged, thereby generating a sensor housing section 620. A tubular spring 626 is essentially trapped in a floppy section 622, as the diameters of a first section 624 and sensor housing section 620 are larger than the diameter of tubular spring 626. The diameter of sensor housing section 620, as shown by an arrow 628, which represents the full diameter of sensor housing section 620 and not the inner or outer diameter of that section, is large enough that a tubular spring (not shown) can be inserted. In a sixth procedure 592, once the general configuration of the guidewire has been prepared, a sensor 630, coupled with a twisted pair of wires 632, referred to herein as twisted pair 632, are threaded into the guidewire, in the direction of an arrow 640, through a sensor housing section 636. It is noted that twisted pair 632 may be long, as represented by set of lines 634. Once sensor 630 and twisted pair 632 are threaded through the guidewire, a plug 638 is inserted over the opening of sensor housing section 636 in the direction of an arrow 642. As mentioned above, the floppy section (not shown) of the guidewire may be covered with a glue to cover any section of twisted pair of wires 632 which are exposed. Twisted pair of wires 632 can then be coupled with an interconnect, thereby generating a finished, functional guidewire, substantially similar in configuration to guidewire 470, (FIG. 5A) and in functionality to guidewire 100 (FIG. 1A). Additionally, an elastic polymer layer may be applied to the distal end of the guidewire. This elastic polymer layer is typically a heat shrink tube having a thickness in the order of a few microns, which provides a slick, smooth, lubricious surface.

Figure 7:
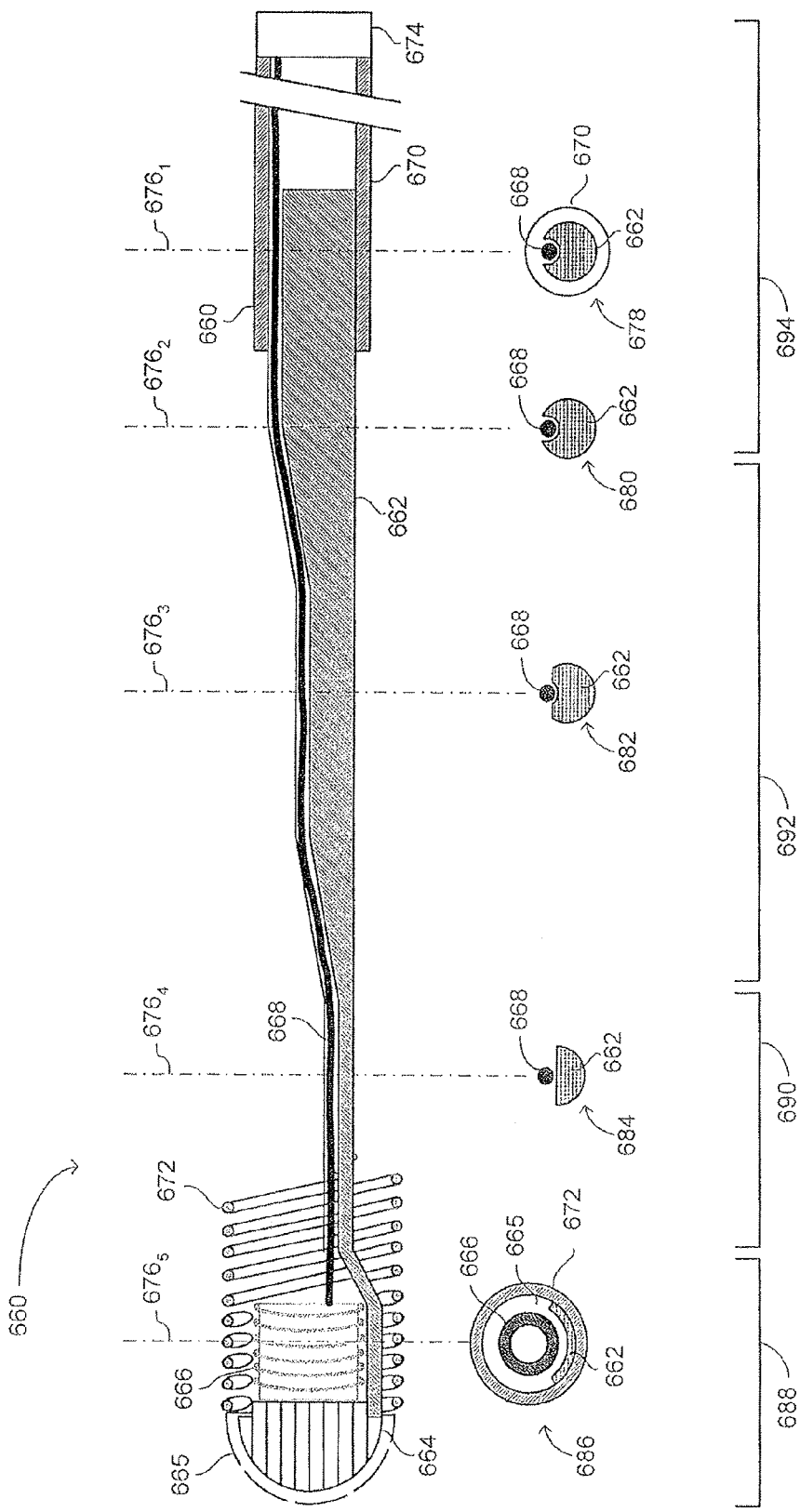
FIG. 7 is a schematic illustration of a cross sectional view of a guidewire, constructed and operative in accordance with another embodiment of the disclosed technique.

Reference is now made to FIG. 7, which is a schematic illustration of a cross sectional view of a guidewire generally referenced 660, constructed and operative in accordance with another embodiment of the disclosed technique. Guidewire 660 includes a grooved corewire 662, a plug 664, a sensor 666, a twisted pair of wires 668, referred to herein as twisted pair 668, a tubular proximal end 670 and a tubular spring 672. Grooved corewire 662 is made of metal (e.g., Stainless Steel, Nitinol). Sensor 666 is sensor capable of measuring scalar values such as pressure and temperature as well as vector values such as position and orientation of a magnetic field. For example, sensor 66 is a coil sensor capable of measuring the strength and orientation of a magnetic field. Guidewire 660 can be coupled with an interconnect 674. Twisted pair 668 are coupled with sensor 666 and with interconnect 674. Plug 664 is coupled with the distal tip section 688 of guidewire 660. Tubular spring 670 is placed around distal sections 688 and 690 of guidewire 660. Grooved corewire 662 is coupled with tubular proximal end 670 (e.g., by bonding or welding).

In FIG. 7, dash-dot lines 676$_1$, 676$_2$, 676$_3$, 676$_4$ and 676$_5$ represent lateral cross-sections of guidewire 660. Along section 694, the diameter of grooved corewire 694 remains substantially constant and is in the order of hundreds of micrometers. In first cross-section 678, the diameter of grooved corewire 662 has an initial outer diameter and is inserted into tubular proximal end 670. Twisted pair 668 are placed within a groove along grooved corewire 662. It is noted that although twisted pair 668 is an unshielded twisted pair, tubular spring 672 may provide electrical shielding for twisted pair 668. In second cross-section 680 the diameter of grooved corewire 662 has an initial outer diameter and twisted pair 668 are placed within a groove along grooved corewire 662. However, grooved corewire 662 is no longer within tubular proximal end 670.

Along section 692 of guidewire 660, the diameter of grooved corewire 662 is gradually reduced. Furthermore, the shape of the lateral cross-section of grooved corewire 662 gradually changes. In third cross-section 682 the shape of the lateral cross-section of grooved corewire 662 is that of a semi-circle. Furthermore, in third cross-section 682, the diameter of grooved corewire 662 is smaller than in first and second cross-sections 678 and 680. Along section 690, the diameter of grooved corewire 660 is substantially constant, however, this diameter is smaller than the diameter shown in cross-section 682. In forth cross-section 684 the shape of lateral cross-section of grooved corewire 662 is that of circular segment. Fifth cross-section 686 is a cross section of the distal tip of guidewire 670 (i.e. section 688). Along section 188 the residual volume between sensor 666 and tubular spring 672 is filled with a polymer bond 665, thus securing the sensor in place. In FIG. 7, the distal end of guidewire 670 is formed, according to the disclosed technique, in a manner such that it exhibits increased flexibility over the flexibility of guidewires 100 and 220. Thus the distal tip of guidewire 670 exhibits substantial maneuverability.

Figure 8A:
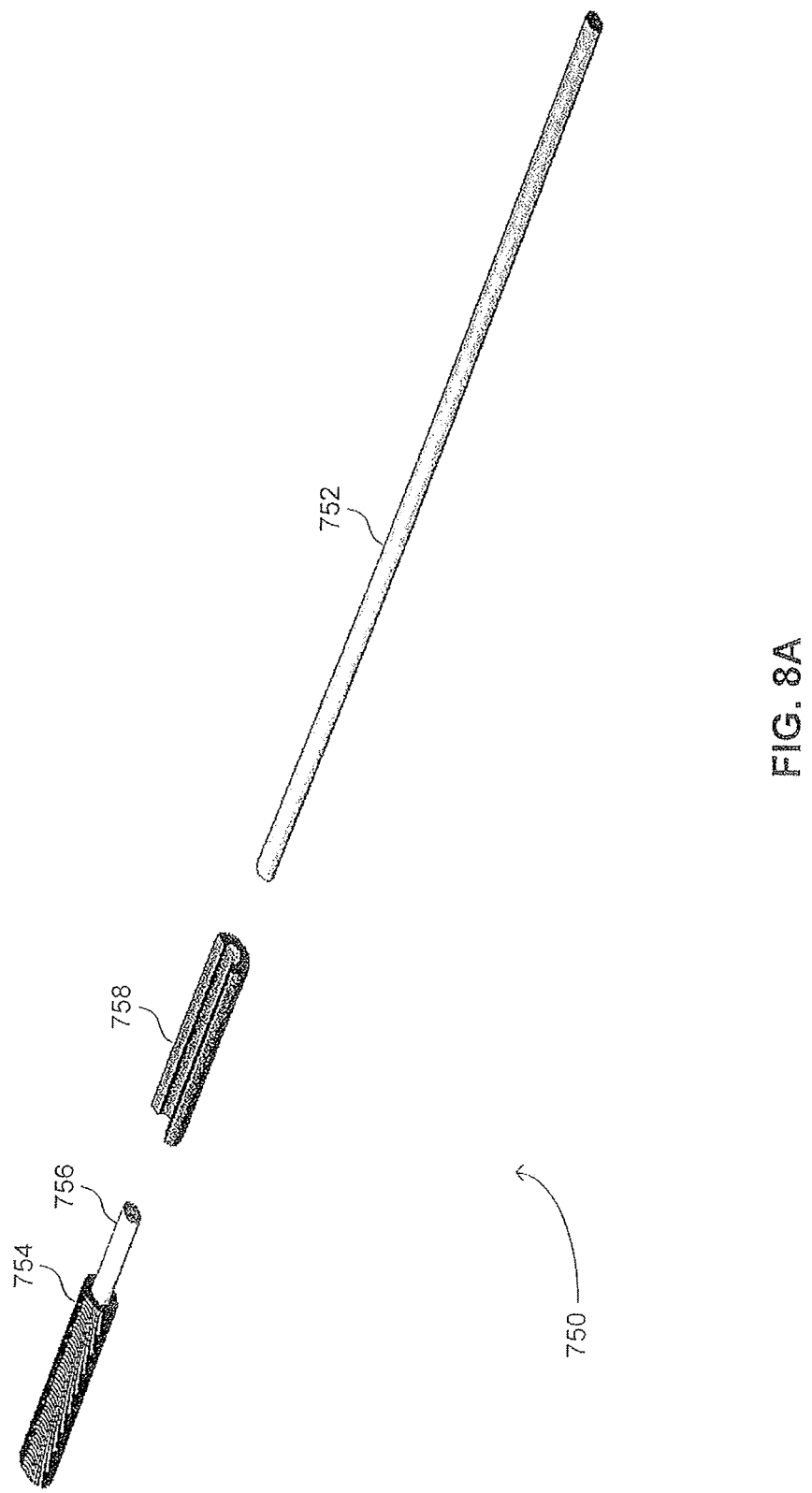
FIG. 8A is a schematic perspective exploded illustrations of a guidewire, constructed and operative in accordance with a further embodiment of the disclosed technique.
Figure 8B:
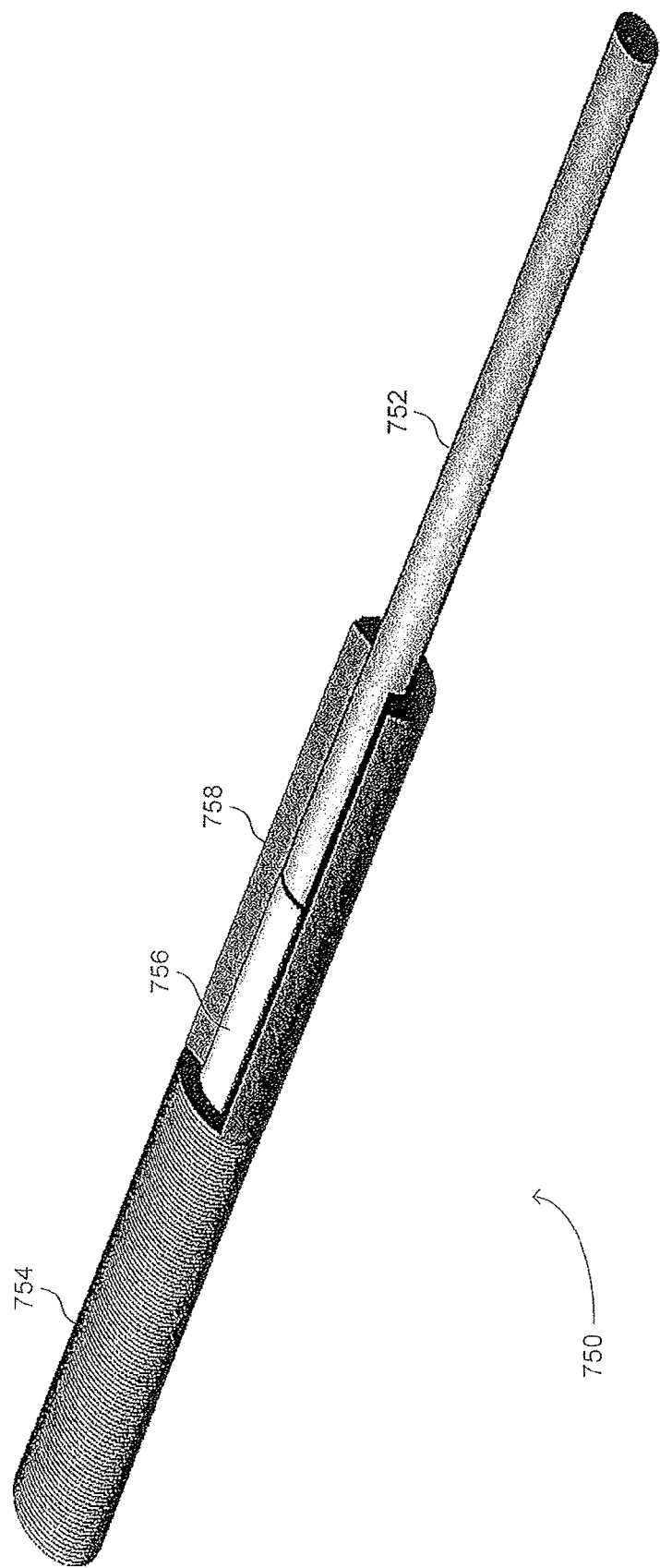
FIG. 8B is a schematic perspective illustration of a guidewire, constructed and operative in accordance with a further embodiment of the disclosed technique, at an intermediate stage of assembly.
Figure 8C:
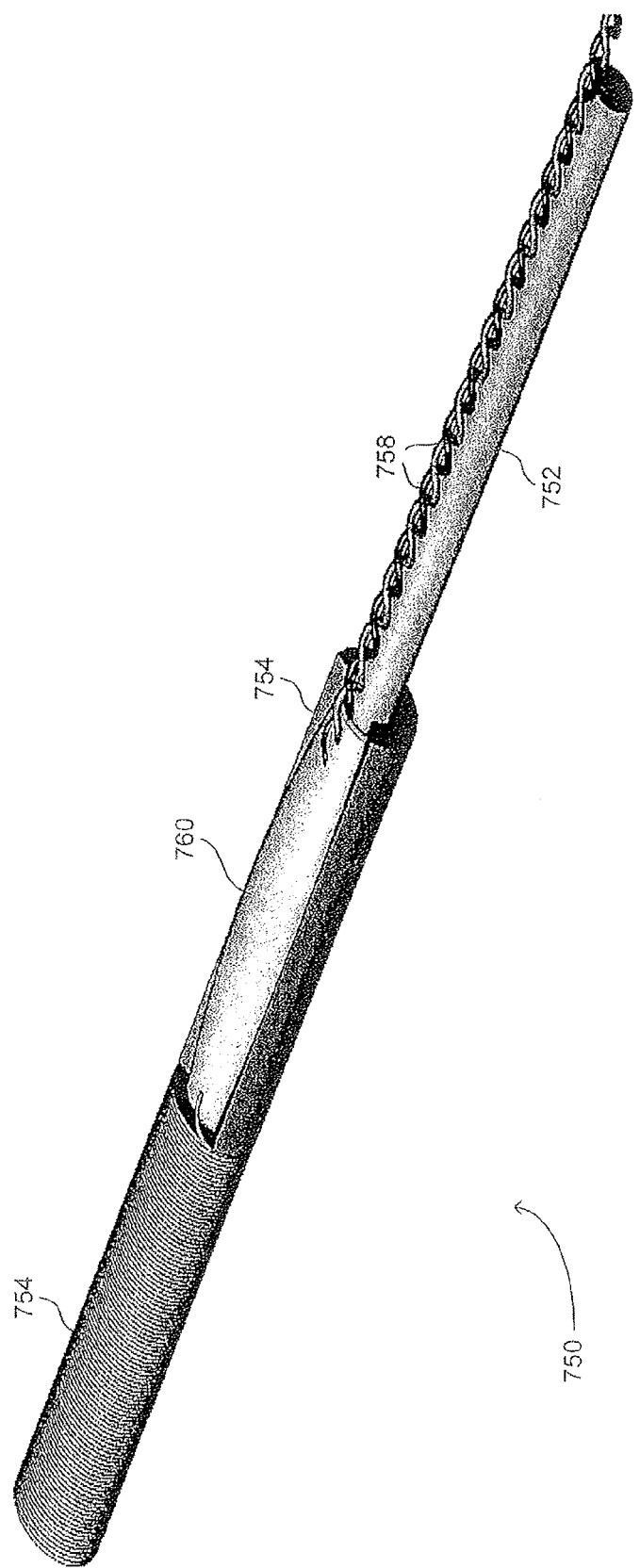
FIG. 8C is a schematic perspective illustration of a guidewire, constructed and operative in accordance with a further embodiment of the disclosed technique, at a final stage of assembly.

Reference is now made to FIGS. 8A, 8B and 8C, which are schematic perspective illustration of a guidewire, generally reference 750, constructed and operative in accordance with a further embodiment of the disclosed technique. FIG. 8A a schematic perspective exploded illustrations of the guidewire 750. Guidewire 750 includes a corewire 752, a sensor 754, a sensor core 756 and a coupler 758. Sensor 754 is coupled with a sensor core 756. The length of sensor core 756 is larger than the length of sensor 754. Thus, when sensor 754 is coupled with sensor core 756, sensor 754 covers only a portion of sensor core 756 such that sensor core 756 extends from one side of sensor 754. The lengths of sensor 754 and sensor core 756 are on the order of a few millimeters. In FIGS. 8A, 8B and 8C, sensor 754 is a coil sensor capable of measuring the strength and orientation of a magnetic field. In general, coil sensor can have a thickness on the order of a few hundred micrometers (e.g., 250 μm). Corewire 752 and sensor core 756 exhibit substantially the same diameter (e.g., on the order of hundreds of micrometers). Coupler 758 is a hollow tube with a part of the wall thereof removed along the length of coupler 758. The inner diameter of coupler 758 is substantially similar to the diameters of corewire 752 and sensor core 756.

FIG. 8B a schematic perspective illustration of the guidewire 750 at an intermediate stage of assembly. In FIG. 8B, corewire 752 is inserted into one side of coupler 754. The portion sensor core 756 that is not covered by sensor 754 is inserted into the other side of coupler 754. FIG. 8C a schematic perspective illustration of the guidewire 750 at a final stage of assembly. In FIG. 8C, a twisted pair of wires 758 are coupled with sensor 754 by a coupling material 760. Twisted par 758 may be coupled, at the proximal end of the guidewire with an interconnect (not shown) which enables twisted pair 758, and thus sensor 754, to be coupled with other devices, such as a computer, a power source, a device measuring magnetic field strength and orientation and the like. Guidewire 750 may be further covered with a thin elastic polymer layer (not shown) over a portion of the length thereof. This polymer layer is typically a heat shrink tube of a few microns thickness, which provides a slick, smooth and lubricious surface.

A tubular spring (not shown) may be placed around a portion the distal section of guidewire 750. This tubular spring is a tube exhibiting lateral flexibility (i.e., perpendicular to the central axis of the tube) made of a metal (e.g., Stainless Steel, Platinum, Iridium, Nitinol), a flexible polymer tube or a braided or coiled plastic tube. The tubular spring maintains the outer diameter of guidewire 750 over the length thereof and supports compressive loads and resists buckling of the guidewire without substantially increasing torsional and bending stiffness.

Figure 8D:
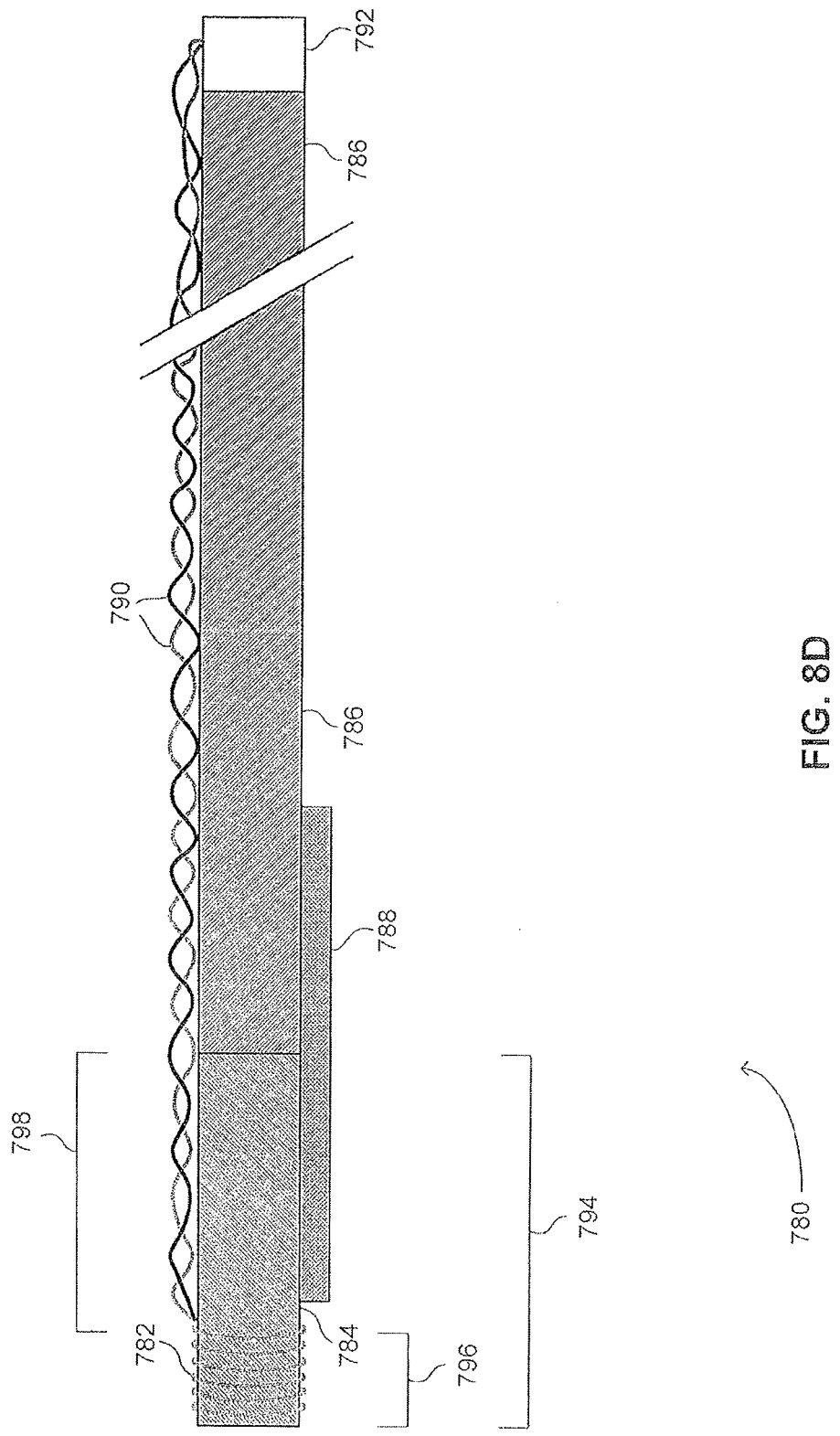
FIG. 8D is a schematic illustration of a cross sectional view of a guidewire, constructed and operative in accordance with another embodiment of the disclosed technique.

Reference is now made to FIG. 8D which is a schematic illustration of a cross sectional view of a guidewire, generally reference 780, constructed and operative in accordance with another embodiment of the disclosed technique. Guidewire 780 includes a core wire 786, a sensor 782, a sensor core 784, a coupler 788, a twisted pair of wires 790 and an interconnect 792. Sensor 782 is coupled with sensor core 784. The length of sensor core 784, delineated by a bracket 794, is larger than the length of sensor 782, delineated by a bracket 796. Thus, when sensor 782 is coupled with sensor core 784, sensor 754 covers only a portion of sensor core 756. The portion of sensor core 784 that is not covered sensor 782, delineated by a bracket 798, extends from one side of sensor 782. Corewire 786 and sensor core 784 exhibit substantially the same diameter (e.g., on the order of hundreds of micrometers). Coupler 788 is a hollow tube with a part of the wall thereof removed along the length of coupler 788. The inner diameter of coupler 788 is substantially similar to the diameters of corewire 786 and sensor core 784.

Corewire 786 is inserted into one side of coupler 788. The portion of sensor core 756 delineated by bracket 798 (i.e., the portion of sensor core 784 that is not covered by sensor 782) is inserted into the other side of coupler 788. Twisted pair of wires 790 are coupled with sensor 782 and with an interconnect 780 which enables twisted pair 790, and thus sensor 782 to be coupled with other devices. As described above (i.e., in conjunction with FIGS. 8A, 8B and 8C regarding guidewire 750), guidewire 780 may be further covered with a thin elastic polymer layer (not shown). Furthermore, a tubular spring (not shown) may be placed around a portion the distal section of guidewire 780.

Figure 9B:
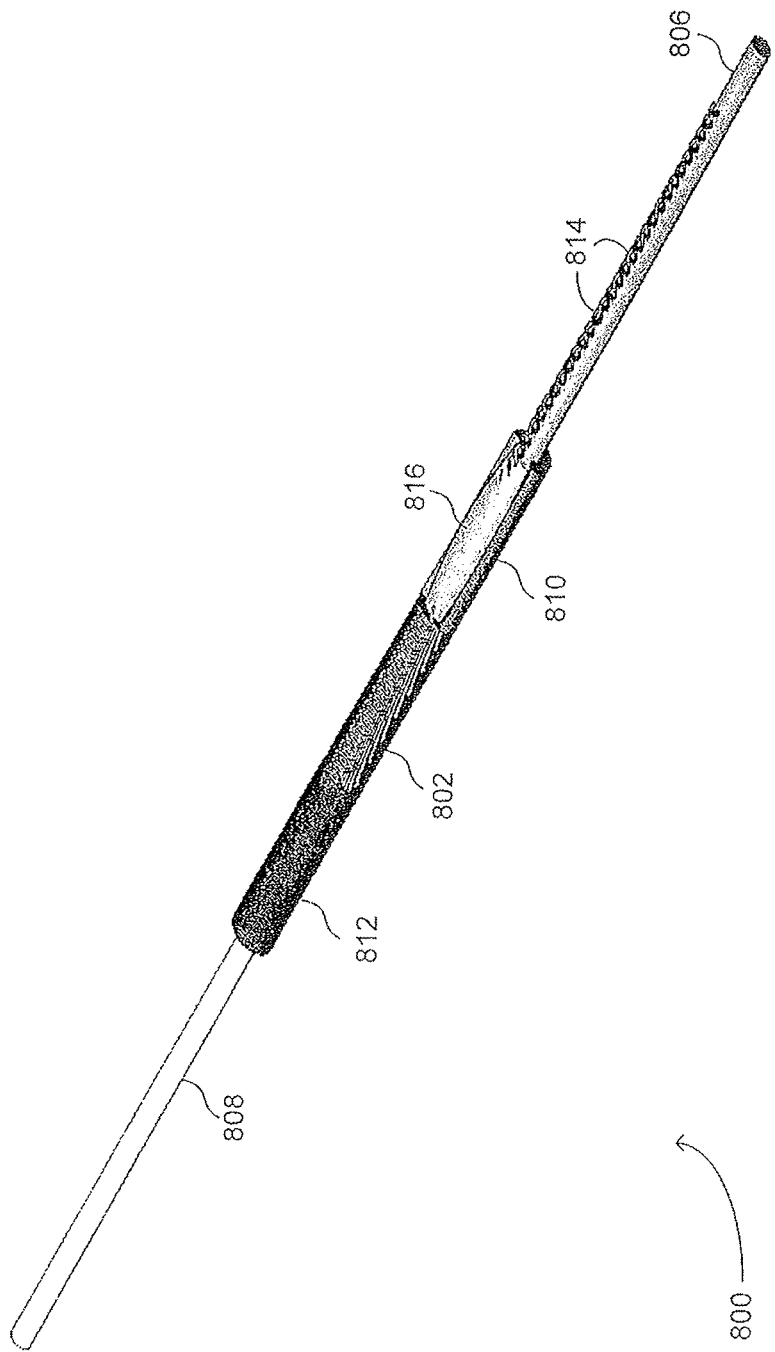
FIG. 9B is a schematic perspective illustration of a guidewire constructed and operative in accordance with a further embodiment of the disclosed technique, at a final stage of assembly.

Reference is now made to FIGS. 9A and 9B, which are schematic perspective illustrations of a guidewire, generally referenced 800, constructed and operative in accordance with a further embodiment of the disclosed technique. FIG. 9A a schematic perspective exploded illustrations of the guidewire 800. Guidewire 800 includes a first corewire 806, a second corewire 808, a sensor 802, a sensor core 804 a first 5 coupler 810 and a second coupler 812. Sensor 808 is coupled with a sensor core 804. The length of sensor core 804 is larger than the length of sensor 802. Thus, when sensor 802 is coupled with sensor core 804, sensor 802 covers only a portion of sensor core 756 such that sensor core 804 extends from both sides of sensor 802. The lengths of sensor 802 10 and sensor core 802 are on the order of a few millimeters. In FIGS. 9A and 9B sensor 802 is a coil sensor. However, sensor 802 may be any other type of sensor capable of measuring scalar of vector values.

First and second corewires 806 and 808 and sensor core 804 exhibit substantially the same diameter (e.g., on the order of hundreds of micrometers). First coupler 810 is a hollow tube with a part of the wall thereof removed along the length of first coupler 810. Second coupler 812 is a whole hollow tube. The inner diameters of first coupler 810 and second coupler 812 are substantially similar to the diameters of first and second corewires 806 and 808 and the diameter of sensor core 804.

FIG. 9B is a schematic perspective illustration of the guidewire 800 at a final stage of assembly. In FIG. 9B, a twisted pair of wires 814 are coupled with sensor 802 by a coupling material 816. First corewire 806 is inserted into one side of first coupler 810. One side of sensor core 804 is inserted into the other side of first coupler 810. The other side of sensor core 804 is inserted into one side of second coupler 812. Second corewire 808 is inserted into the other side of coupler 812. Thus, sensor 802 is positioned anywhere along the length of guidewire 800.

Twisted pair 814 may be coupled, at the proximal end of the guidewire with an interconnect (not shown) which enables twisted pair 814, and thus sensor 802, to be coupled with other devices. Similarly to as describe above, guidewire 800 may also be covered with a thin elastic polymer layer (not shown) over a portion of the length thereof. Furthermore, a tubular spring (not shown) may be placed around a portion the distal section of guidewire 800.

It will be appreciated by persons skilled in the art that the disclosed technique is not limited to what has been particularly shown and described hereinabove. Rather the scope of the disclosed technique is defined only by the claims, which follow.

What is claimed is:

1. A medical device comprising:
    an elongate assembly, comprising:
        a proximal portion having a first outer diameter;
        an intermediate portion having a second outer diameter, said second outer diameter smaller than said first outer diameter; and
        a distal portion having a third outer diameter, said third outer diameter larger than said second outer diameter, wherein said proximal portion, intermediate portion, and distal portion define an axis;
    a coil sensor, disposed within said distal portion, comprising a coil of wire wound substantially around said axis, said coil configured to produce an electrical signal indicative of a characteristic of a magnetic field in which said coil is disposed; and
    a tubular spring around said intermediate portion.

2. The medical device of claim 1, further comprising a non-traumatic plug coupled with said distal portion.

3. The medical device of claim 1, wherein said first diameter and said third diameter are substantially equal.

4. The medical device of claim 1, wherein said tubular spring has a spring outer diameter, said spring outer diameter substantially equal to one or more of said first outer diameter and said third outer diameter.

5. The medical device of claim 1, wherein said tubular spring is disposed around substantially the entirety of said intermediate portion.

6. The medical device of claim 5, wherein substantially all of said intermediate portion has said second outer diameter.

7. The medical device of claim 1, wherein the medical device comprises a guidewire.

8. A medical device comprising:
    an elongate assembly, comprising:
        a first axial portion having a first outer diameter; and
        a second axial portion having a second outer diameter, said second outer diameter larger than said first outer diameter, wherein said first axial portion and said second axial portion define an assembly axis;
    a coil sensor, disposed within said second axial portion, comprising a coil of wire having a plurality of turns that each extend circumferentially around a sensor axis that is substantially parallel with said assembly axis, said coil configured to produce an electrical signal indicative of a characteristic of a magnetic field in which said coil is disposed; and
    a tubular spring around substantially all of said first axial portion.

9. The medical device of claim 8, further comprising a non-traumatic plug coupled with said distal portion.

10. The medical device of claim 8, wherein said tubular spring has a spring outer diameter that is substantially equal to said first outer diameter.

11. The medical device of claim 10, wherein said first axial portion is immediately adjacent to said second axial portion.

12. The medical device of claim 8, wherein said spring is made of one or more of metal and a flexible polymer tube.

13. The medical device of claim 8, wherein said coil sensor has a radial thickness of between two hundred micrometers and three hundred micrometers.

14. The medical device of claim 8, wherein the medical device comprises a guidewire.

15. A medical device comprising:
   an elongate assembly, comprising:
      a proximal portion having a first outer diameter;
      an intermediate portion having a second outer diameter; and
      a distal portion having a third outer diameter, wherein said proximal portion, intermediate portion, and distal portion define an axis;
      a coil sensor, disposed within said distal portion, comprising a coil of wire wound substantially around said axis, said coil configured to produce an electrical signal indicative of a characteristic of a magnetic field in which said coil is disposed; and
      a tubular spring around said intermediate portion, said tubular spring having a spring outer diameter, wherein said first outer diameter, said third outer diameter, and said spring outer diameter are substantially equal.

16. The medical device of claim 15, further comprising a non-traumatic plug coupled with said distal portion.

17. The medical device of claim 15, wherein said spring is made of one or more of metal and a flexible polymer tube.

18. The medical device of claim 15, wherein said distal portion is immediately adjacent to said intermediate portion.

19. The medical device of claim 18, wherein said proximal portion is immediately adjacent to said intermediate portion.

20. The medical device of claim 15, wherein the medical device comprises a guidewire.

* * * * *